(12) United States Patent
Pourquie et al.

(10) Patent No.: US 11,390,850 B2
(45) Date of Patent: Jul. 19, 2022

(54) GENERATION OF BROWN ADIPOSE TISSUE FROM PLURIPOTENT STEM CELLS IN VITRO

(71) Applicant: The Brigham and Women's Hospital, Inc., Boston, MA (US)

(72) Inventors: Olivier Pourquie, Brookline, MA (US); Jerome Chal, Boston, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 684 days.

(21) Appl. No.: 16/311,852

(22) PCT Filed: Jun. 23, 2017

(86) PCT No.: PCT/US2017/039011
§ 371 (c)(1),
(2) Date: Dec. 20, 2018

(87) PCT Pub. No.: WO2017/223457
PCT Pub. Date: Dec. 28, 2017

(65) Prior Publication Data
US 2019/0203177 A1    Jul. 4, 2019

Related U.S. Application Data

(60) Provisional application No. 62/470,656, filed on Mar. 13, 2017, provisional application No. 62/354,276, filed on Jun. 24, 2016.

(51) Int. Cl.
| | |
|---|---|
| *C12N 5/077* | (2010.01) |
| *A61K 35/35* | (2015.01) |
| *G01N 33/50* | (2006.01) |
| *A61P 5/00* | (2006.01) |
| *C12Q 1/6881* | (2018.01) |
| *A61K 49/00* | (2006.01) |

(52) U.S. Cl.
CPC ............ *C12N 5/0653* (2013.01); *A61K 35/35* (2013.01); *A61K 49/0008* (2013.01); *A61P 5/00* (2018.01); *C12Q 1/6881* (2013.01); *G01N 33/5023* (2013.01); *G01N 33/5041* (2013.01); *G01N 33/5044* (2013.01); *C12N 2500/25* (2013.01); *C12N 2501/105* (2013.01); *C12N 2501/115* (2013.01); *C12N 2501/12* (2013.01); *C12N 2501/155* (2013.01); *C12N 2501/385* (2013.01); *C12N 2501/39* (2013.01); *C12N 2501/395* (2013.01); *C12N 2501/415* (2013.01); *C12N 2506/02* (2013.01); *C12N 2506/45* (2013.01); *C12N 2533/54* (2013.01); *C12Q 2600/158* (2013.01); *G01N 2800/044* (2013.01)

(58) Field of Classification Search
None
See application file for complete search history.

(56) References Cited

U.S. PATENT DOCUMENTS

| | | |
|---|---|---|
| 2015/0030662 A1 | 1/2015 | Raghunath et al. |
| 2016/0303100 A1 | 10/2016 | Boss et al. |
| 2017/0014455 A1* | 1/2017 | Nie ...................... A61K 31/192 |

FOREIGN PATENT DOCUMENTS

WO    WO2013030243    3/2013

OTHER PUBLICATIONS

Ahfeldt et al, "Programming human pluripotent stem cells into white and brown adipocytes," 2012, Nat. Cell. Biol., 14, 209-219.
Atit et al., "Beta-catenin activation is necessary and sufficient to specify the dorsal dermal fate in the mouse," Dev Biol., 2006, 296:164-176.
Barberi et al, "Derivation of multipotent mesenchymal precursors from human embryonic stem cells," PLoS medicine, 2005, 2:e161.
Billon & Dani, "Developmental origins of the adipocyte lineage: new insights from genetics and genomics studies," Stem cell reviews, 2012, 8:55-66.
Boon et al, "Tracing human brown fat," Nat Med, 2015, 21:667-668.
Borensztein et al, "Double Myod and Igf2 inactivation promotes brown adipose tissue development by increasing Prdm16 expression," FASEB J., 2012, 26:4584-4591.
Buckingham, "Myogenic progenitor cells and skeletal myogenesis invertebrates," Curr. Opin. Genet. Dev., 2006, 16:525-532.
Chal et al, "Differentiation of pluripotent stem cells to muscle fiber to model Duchenne muscular dystrophy," Nat. Biotechnol., 2015, 33:962-969.
Chal et al, "Generation of human muscle fibers and satellite-like cells from human pluripotent stem cells in vitro," Nat. Protoc., 2016, 11(10):1833-1850.
Choi et al, "Concordant but Varied Phenotypes among Duchenne Muscular Dystrophy Patient-Specific Myoblasts Derived using a Human iPSC-Based Model," Cell Rep., 2016, 7:15(10):2301-2312.
Crisan et al., "A reservoir of brown adipocyte progenitors in human skeletal muscle," Stem Cells, 2008, 26:2425-2433.
Cristancho & Lazar, "Forming functional fat: a growing understanding of adipocyte differentiation," Nat. Rev. Mol. Cell. Biol., 2011, 12:722-734.

(Continued)

*Primary Examiner* — Emily A Cordas
(74) *Attorney, Agent, or Firm* — Fish & Richardson P.C.

(57) ABSTRACT

A population of Brown adipose tissue (BAT) cells generated from embryonic stem cells (ES) or induced pluripotent stem cells (iPS), called iBAT, the use thereof, methods to obtain iBAT by directed differentiation of ES/iPS, and media compositions to obtain iBAT.

6 Claims, 9 Drawing Sheets
(7 of 9 Drawing Sheet(s) Filed in Color)

(56) References Cited

OTHER PUBLICATIONS

Dani et al, "Differentiation of embryonic stem cells into adipocytes in vitro," J. Cell. Sci., 1997, 11:1279-1285.
Doan-Xuan et al, "High content analysis of differentiation and cell death in human adipocytes," Cytometry, 2013, A83L933-943.
Fawcett, "A comparison of the Histological Organization and cytochemical reactions of brown and white adipose tissues," Journal of Morphology, 1952, 90:365-405.
Feng et al., "Human Adipose Dynamics and Metabolic Health," Annals of New York Academy of Sciences, 2013, 1281: 160-177.
Hadadeh et al, "The plasminogen activation system modulates differently adipogenesis and myogenesis of embryonic stem cells," PLoS ONE, 2012, e49065.
Hafner & Dani, "Human induced pluripotent stem cells: A new source for brown and white adipocytes," World Journal of Stem Cells, 2014, 6:467-472.
Hafner et al, "Brown-like adipose progenitors derived from human induced pluripotent stem cells: Identification of critical pathways governing their adipogenic capacity," Sci. Rep., 2016, 6:32490.
Harms & Seale, "Brown and beige fat: development, function and therapeutic potential," Nat. Med., 2013, 19:1252-1263.
Hosoyama et al, "Derivation of myogenic progenitors directly from human pluripotent stem cells using a sphere-based culture," Stem Cells Transl. Med., 2014, 3:(5):564-74.
Hwang et al, "Directed in vitro myogenesis of human embryonic stem cells and their in vivo engraftment," PLoS ONE, 2013, 8:e72023.
International Preliminary Report on Patentability in International Application No. PCT/US2017/039011, dated Dec. 25, 2018, 7 pages.
International Search Report and Written Opinion in International Application No. PCT/US2017/039011, dated Sep. 25, 2017, 10 pages.
Kajimura et al, "Initiation of myoblast to brown fat switch by a PRDM16-C/EBP-beta transcriptional complex," 2009, Nature, 460:1154-1158.
Kajimura et al, "Transcriptional control of brown fat development," Cell Metab., 2010, 11:257-262.
Kazantzis et al, "PAZ6 cells constitute a representative model for human brown pre-adipocytes," Frontiers in endocrinology, 2012, 3:13.
Lee et al, "Identification of Small Molecules Which Induce Skeletal Muscle Differentiation in Embryonic Stem Cells via Activation of the Wnt and Inhibition of Smad2/3 and Sonic Hedgehog Pathways," Stem Cells, 34:299-310.
Lee et al, "Serum replacement with a growth factor-free synthetic substance in culture medium contributes to effective establishment of mouse embryonic stem cells of various origins," Fertility and Sterility, 2006, 86:1137-1145.
Lepper & Fan, "Inducible lineage tracing of Pax7-descendant cells reveals embryonic origin of adult satellite cells," Genesis, 2010, 48(7):424-436.
Liu et al., "Brown Adipose Tissue Transplantation Reverses Obesity in Ob/Ob Mice," Endocrinology, 2015, 156:2461-2469.
Loh et al., "Mapping the pairwise choices leading from pluripotency to human bone, heart and other mesoderm cell-types," Cell, 2016, 14:166:(2):451-467.
Mahmood et al, "Enhanced differentiation of human embryonic stem cells to mesenchymal progenitors by inhibition of TGF beta/activin/nodal signaling using SB-431542," J. Bone. Miner. Res., 25:1216-1233.
Mohsen-Kanson et al, "Differentiation of human induced pluripotent stem cells into brown and white adipocytes: role of Pax3," Stem Cells, 2014, 32:1459-1467.

Napolitano & Fawcett, "The fine structure of brown adipose tissue in the newborn mouse and rat," The Journal of Biophysical and Biochemical Cytology, 1958, 4:685-692.
Nishio & Saeki, "Differentiation of human pluripotent stem cells into highly functional classical brown adipocytes," Methods Enzymol, 2014, 537:177-197.
Nishio et al., "Production of functional classical brown adipocytes from human pluripotent stem cells using specific hemopoietin cocktail without gene transfer," Cell Metab., 2012, 16:394-406.
Petrovic et al., "Chronic Peroxisome Proliferator-actlvated Receptor Gamma (PPARgamma) Activation of Epididymally Derived White Adipocyte Cultures Reveals a Population of Thermogenlcally Competent, UCPI-containing Adipocytes Molecularly Distinct from Classic Brown Adipocytes," The Journal of Biological Chemistiy, Dec. 2009, 285: 7153-7164.
Rajakumari et al, "EBF2 determines and maintains brown adipocyte identity," Cell Metab., 2013, 17:562-574.
Sakurai et al., "Bidirectional induction toward paraxial mesodermal derivatives from mouse ES cells in chemically defined medium," Stem Cell Res., 2009, 3:157-169.
Sakurai et al., "In vitro modeling of paraxial and lateral mesoderm differentiation reveals early reversibility," Stem Cells, 2006, 24:575-586.
Sakurai et al., "In vitro modeling of paraxial mesodermal progenitors derived from induced pluripotent stem cells," PLoS ONE, 2012, 7:e47078.
Sanchez-Gurmaches & Guertin, "Adipocyte lineages: tracing back the origins of fat," Biochim. Biophys. Acta., 2014, 1842:340-351.
Sanchez-Gurmaches & Guertin, "Adipocytes arise from multiple lineages that are heterogeneously and dynamically distributed," Nature Communications., 2014, 5:4099.
Seale & Lazar, "Brown fat in humans: turning up the heat on obesity," Diabetes, 2009, 58:1482-1484.
Seale et al., "PRDM16 controls a brown fat/skeletal muscle switch," Nature, 2008, 454:961-967.
Seale et al., "Transcriptional control of brown adipocyte development and physiological function—of mice and men," Genes Dev., 2009, 23:788-797.
Seale et al, "Transcriptional control of brown fat determination by PRDM16," Cell Metab., 2007, 6:38-54.
Sharma et al, "Brown fat determination and development from muscle precursor cells by novel action of bone morphogenetic protein 6," PLoS ONE, 2014, 9:e92608.
Shelton et al, "Derivation and Expansion of PAX7-Positive Muscle Progenitors from Human and Mouse Embryonic Stem Cells," Stem Cell Reports, 2014, 9:3:(3): 516-529.
Timmons et al, "Myogenic gene expression signature establishes that brown and white adipocytes originate from distinct cell lineages," Proc. Natl. Acad. Sci. USA, 2007, 104:4401-4406.
Unser et al, "3D brown adipogenesis to create "Brown-Fat-in-Microstrands"." Biomaterials, 2016, 75:123-134.
Villarroya & Giralt, "The Beneficial Effects of Brown Fat Transplantation: Further Evidence of an Endocrine Role of Brown Adipose Tissue," Endocrinology, 2015, 156:2368-2370.
Wang et al, "Ebf2 is a selective marker of brown and beige adipogenic precursor cells," Proc. Natl. Acad. Sci. USA, 2014, 111:14466-14471.
Whittle et al, "Using brown adipose tissue to treat obesity—the central issue," Trends in Molecular Medicine, 2011, 17:405-411.
Xi et al, "In Vivo Human Somitogenesis Guides Somite Development from hPSCs," Cell Rep., 2017, 7:18(6):1573-1585.
Xue et al, "Clonal analyses and gene profiling identify genetic biomarkers of the thermogenic potential of human brown and white preadipocytes," Nat. Med., 2015, 21:760-768.
Yamamoto et al, "The differentiation of early embryonic stem cells into adipocytes-like cells," Human Cell, 2003, 16:117-122.

* cited by examiner

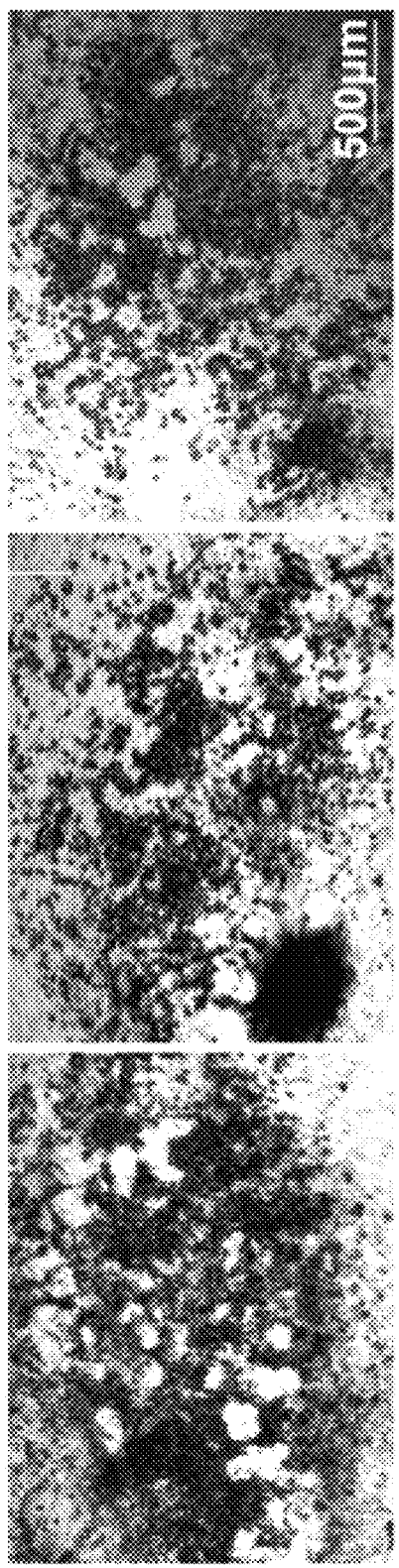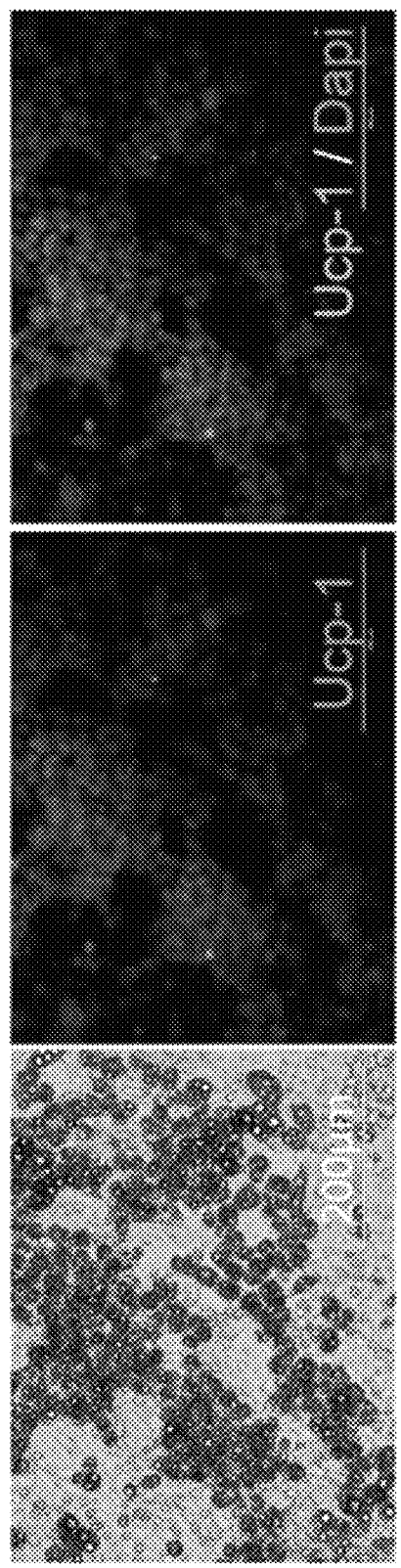
FIG. 4A
FIG. 4B

GENERATION OF BROWN ADIPOSE TISSUE FROM PLURIPOTENT STEM CELLS IN VITRO

CLAIM OF PRIORITY

This application is a § 371 national stage application of International Application No. PCT/US2017/039011, filed on Jun. 23, 2017, which claims the benefit of U.S. Provisional Patent Application Ser. No. 62/354,276, filed on Jun. 24, 2016, and Ser. No. 62/470,656, filed on Mar. 13, 2017. The entire contents of the foregoing are hereby incorporated by reference.

TECHNICAL FIELD

In part, the present disclosure provides a population of Brown adipose tissue (BAT) cells generated from embryonic stem cells (ES) or induced pluripotent stem cells (iPS), called iBAT, the use thereof, methods to obtain iBAT by directed differentiation of ES/iPS, and media compositions to obtain iBAT.

BACKGROUND

Histologically, adipose tissue is composed of 2 main types: a predominant, lipid-rich White adipose tissue (WAT) and a localized, mitochondria-rich Brown adipose tissue (BAT) (Cristancho and Lazar, 2011). WAT is key in maintaining the body's energy and metabolic homeostasis, through lipid storage and endocrine functions and it is the tissue which undergoes a dramatic expansion in obese patients. In contrast, BAT is involved in body's homeothermy and plays an opposite function, burning fat through mitochondrial thermogenesis (Harms and Seale, 2013).

SUMMARY

The present inventors have successfully generated BAT from ES/iPS without the need for either cell sorting strategy or genetic manipulation. The population of interest comprises BAT progenitors and mature BAT. It is obtained technically by in vitro directed differentiation of ES/iPS toward the paraxial mesoderm lineage, and further differentiated with specific signaling pathways modulations to generate brown adipose cell progenitors (i.e., adipoblasts) and brown adipocytes with key features of this cell type: high mitochondria density, lipid droplets accumulation (ranging from 0.1 up to hundreds of $\mu m^2$ in surface area according to a rectilinear parallel projection, round (circular) compacted nucleus, expression of Ucp-1; preferably obtained within 2-3 weeks of differentiation. These allows for a possibly unlimited source of BAT, for which there is currently no other established source. The starting material can be mammalian ES/iPS, preferably of human or mouse origin. Thus, describe herein are simple and robust culture methods to generate BAT. The iBAT obtained with these methods could be used, e.g., for in vitro drug screening and/or as a source of cells for cell/metabolic therapy, diabetes and metabolic disorders.

Provided herein are in vitro methods for generating an induced Brown Adipose Tissue (iBAT) cell. The methods include providing a paraxial mesoderm (PAM) cell that expresses at least one of Pax3, Myf5, and Pax7; and culturing the PAM cell in conditions and for a time, preferably two to five weeks, sufficient for the cells to differentiate into iBAT cells that express uncoupling protein 1 (UCP-1). (i) medium comprising effective amounts of each of an HGF signaling pathway activator, an IGF signaling pathway activator, and an FGF signaling pathway activator; and a BMP signaling pathway inhibitor, e.g., an ALK inhibitor, for at least one day, e.g., for two days, followed by culturing in a medium comprising an HGF signaling pathway activator and an IGF signaling pathway activator but lacking a FGF signaling pathway activator; or (ii) medium comprising an FGF signaling pathway inhibitor, e.g., PD173074, and Retinoic acid signaling pathway activator, preferably Retinoic acid, for two to six days, followed by an adipocyte differentiation medium preferably comprising an effective amount of each of serum or a serum replacement supplement (as a substitute for serum), an Insulin signaling pathway activator, an iron-binding glycoprotein that is internalized through Transferrin receptor-mediated endocytosis, a cofactor for anti-oxidants reduction, a methylated xanthine derivative that acts both as a competitive non selective phosphodiesterase inhibitor and a non-selective adenosine receptor antagonist; a non-steroidal non selective inhibitor of the cyclooxygenase and thus an inhibitor of prostaglandin production; a thyroid hormone receptor signaling pathway activator; a synthetic cortisol derivative; and a thiazolidinedione molecule binding to the peroxisome proliferator-activated receptor gamma (PPARγ) nuclear receptor.

In some embodiments, the adipocyte differentiation medium comprises a serum replacement supplement (as a substitute to serum), preferably comprising lipid-rich albumin (such as Knock-out serum replacement (KnockOut™ SR, Gibco™); Insulin-Transferin-Selenium; isobutylmethylxanthine (IBMX); indomethacin, triiodothreonine (T3); dexamethasone; and rosiglitazone.

In some embodiments, the iBAT cell is a multilocular fat cell with a dark or brown coloration in brightfield imaging; adherent or in suspension; has circular compacted nuclei; is enriched for mitochondria; and is enriched in lipid droplets of various sizes ranging from 0.1 $\mu m^2$ to 1000 $\mu m^2$ in surface area according to a rectilinear parallel projection, or ranging from 1 $\mu m^3$ to hundreds or thousands of $\mu m^3$ in volume.

In some embodiments, an iBAT cell generated according to condition (i) comprises numerous lipid droplets of sizes ranging from 0.5 $\mu m^2$ to 1000 $\mu m^2$ in surface area according to a rectilinear parallel projection, or ranging 5 $\mu m^3$ to 10,000 of $\mu m^3$ in volume.

In some embodiments, an iBAT cell generated according to condition (ii) comprises numerous lipid droplets of sizes ranging from 0.1 $\mu m^2$ to 50 $\mu m^2$ in surface area according to a rectilinear parallel projection, or ranging 1 $\mu m^3$ to 100 $\mu m^3$ in volume.

In some embodiments, the methods include culturing the iBAT cells under conditions sufficient for proliferation to occur.

Also provided herein are compositions comprising a population, e.g., a stable population of iBAT cells, prepared by a method described herein, and optionally a physiologically acceptable carrier.

In some embodiments, the carrier comprises a biocompatible semisolid or gel matrix.

In some embodiments, the matrix comprises a hydrogel matrix, e.g., a hyaluronic acid-based hydrogel; collagen/alginate microspheres; or adipose tissue derived soluble extracellular matrix.

Also provided herein are multi-well plates, wherein at least one of the wells of the plate comprises a population of iBAT cells prepared by a method described herein.

Also provided are methods for treating a metabolic disorder in a subject, the method comprising administering a population of iBAT cells prepared by a method described herein.

In some embodiments, the metabolic disorder is diabetes, insulin-resistance, obesity, hypertension, an insulin resistance disorder, or hepatic steatosis.

Also provided herein are methods for identifying a candidate compound for use in treating a metabolic disorder. The methods include providing a population of iBAT cells prepared by a method described herein, e.g., in vitro; contacting the population of iBAT cells with a test compound; determining the ability of the test compound to increase expression of UCP-1, Dio2, Cidea2, FABP4, C/ebpβ, Prdm16, Pgc-1α, Ppar-α, Ebf2 and Thyroid receptor (TR), and/or stimulate proliferation of BAT progenitors, and/or increase fat storage evaluated for example by Oil Red O staining, and/or increase BAT thermogenic activity, and/or increase BAT metabolic activity, e.g., as evaluated by measure of glycolysis, mitochondrial respiration, lipid synthesis, beta-oxidation and mitochondrial uncoupling in the iBAT cells; and selecting as a candidate a compound that increases expression of UCP-1, Dio2, Cidea2, FABP4, C/ebp, Ebf2, and/or Prdm16, and/or stimulates proliferation of BAT progenitors, and/or increases fat storage evaluated for example by Oil Red O staining, and/or increases BAT thermogenic activity, and/or increases BAT metabolic activity, e.g., as evaluated by measure of glycolysis, mitochondrial respiration, lipid synthesis, beta-oxidation and mitochondrial uncoupling.

In some embodiments, the metabolic disorder is diabetes, obesity, insulin-resistance, hypertension, an insulin resistance disorder, or hepatic steatosis.

In some embodiments, the methods include administering the selected candidate compound to an animal model of the metabolic disorder; evaluating an effect of the candidate compound on a parameter of the metabolic disorder in the animal model; and
selecting a candidate compound that improves the parameter of the metabolic disorder in the animal model as a candidate therapeutic compound.

In some embodiments, the metabolic disorder is obesity, and the parameter is weight, and an improvement in the parameter is weight loss.

In some embodiments, the metabolic disorder is diabetes, insulin-resistance, hypertension, an insulin resistance disorder, or hepatic steatosis, and the parameter is blood glucose level, insulin sensitivity, blood pressure or liver enzyme levels; and an improvement in the parameter is improved blood glucose control, improved insulin sensitivity, improved blood pressure control or improved liver enzyme levels.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

This patent or application file contains at least one drawing executed in color. Copies of this patent or patent application publication with color drawing(s) will be provided by the Office upon request and payment of the necessary fee.

FIGS. 4A-C show large fields of brown fat cells (adipoblasts, adipocytes) that can be detected as early as 2 weeks of differentiation (here at day 17 of differentiation) using Method 1 from mouse ES cells. (A) representative differentiated cultures of mouse ESC showing large fields of dark brown fat cells. (B) Staining of the culture for Ucp-1 protein expression showing that the generated brown adipocytes express the uncoupling protein 1 (Ucp-1), a marker specific of BAT cells. Note the multilocular aspect in brightfield view. (C) Higher magnification of the cultures stained for Ucp-1. Note that Ucp-1 staining is specific to cytoplasm. Note the circular, compacted aspect of nuclei (arrowheads) in the multilocular, Ucp-1$^+$ cells, a hallmark of adipocytes. Lipid droplets sizes ranged from 0.5 up to hundreds of μm$^2$ in surface area according to a rectilinear parallel projection.

DETAILED DESCRIPTION

Figure 1:
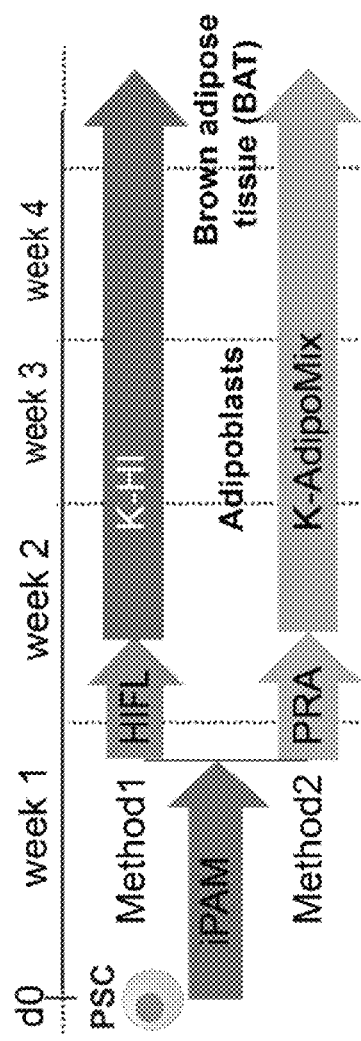
FIG. 1 shows a diagram representing exemplary in vitro directed differentiation strategy to generate Brown fat cells from ES/iPS cells. Differentiation timeline is shown on top. Arrows represent the temporal sequence of media applied to the cultures. In some embodiments, the protocol first relies on the generation of induced paraxial mesoderm (iPAM) according to the method previously described (Chal et al, Nat Biotechnol 33, 962-969, 2015; Chal et al., Nat Protoc. 2016 October; 11(10):1833-50; WO2013030243). The protocol branched at a stage where the common precursors of skeletal muscle and brown fat (Pax3$^+$ anterior PSM/dermomyotomal progenitors) are generated in the culture (in mouse cells, at day 6 of differentiation). Two alternative methods to produce Brown fat cell populations are illustrated with Method 1 relying on the use of HGF and IGF, while Method 2 relies on Retinoic acid (RA), a FGF inhibitor (such as PD173074), followed by an Adipogenic differentiation mixture (AdipoMix). Both methods can be implemented in presence of Fetal bovine serum (1% to 15%) or of a serum replacement supplement.
Figure 2:
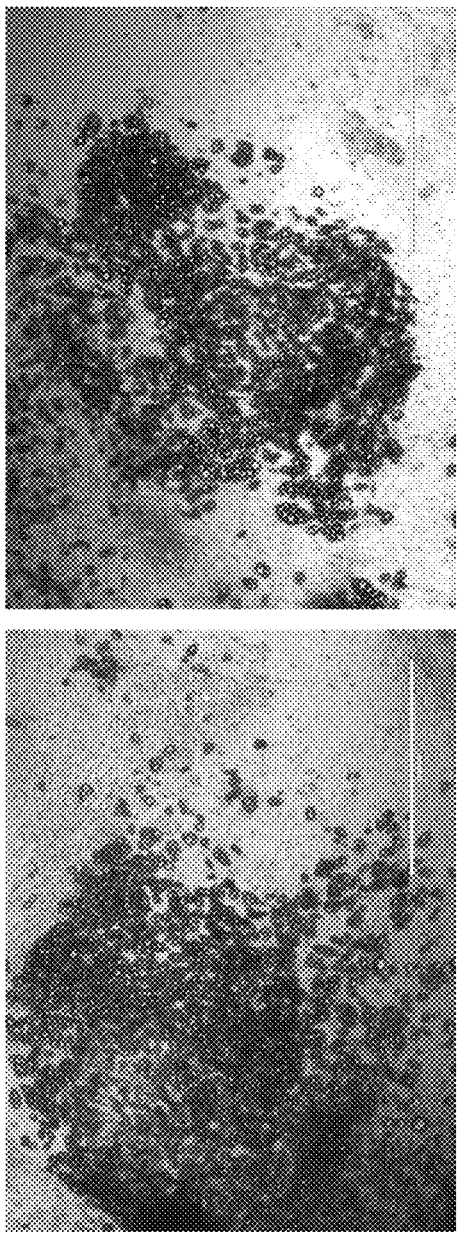
FIG. 2 shows large fields of mouse brown fat cells (adipoblasts, adipocytes) that can be detected as early as 2 weeks of differentiation (here at day 17 of differentiation) using Method 1. BAT-like features of the cell type generated in vitro from PSC are dense, dark brown-colored adipocytes with small lipid droplets (multilocular). Bars, 1000 μm.
Figure 3:
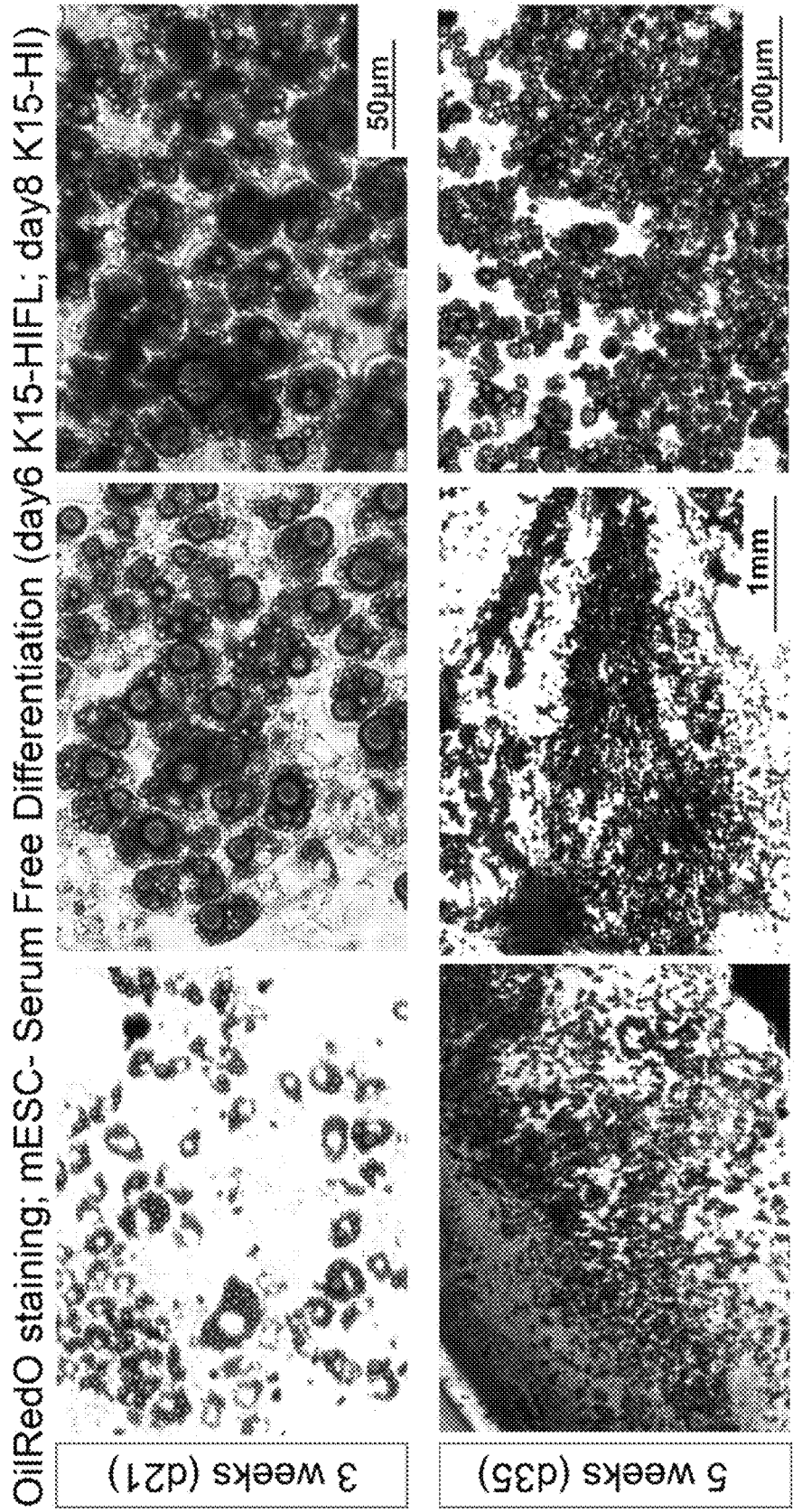
FIG. 3 shows adherent cultures differentiated according to the Method 1 from mouse ES cells and stained with Oil Red O at three and five weeks of differentiation. Lipid droplets (red) carrying fat cells are shown at various magnifications. Note the large fields of multilocular adipocytes.

Brown adipose tissue (BAT) is increasingly becoming an attractive therapeutic target for metabolic control in pathological conditions such as obesity or type 2 diabetes due to its ability to consume excess glucose. In humans, BAT is prevalent in newborns but has also recently been found in adults (Harms and Seale, 2013). Under certain conditions white adipose tissue (WAT) can partially convert to BAT-like tissue ("beige/brite" adipocytes) (Harms and Seale, 2013). The recent years have witnessed a spectacular increase in prevalence of obesity and of type 2 diabetes which now poses a major health challenge worldwide. Increasing the number of brown fat cells and their function in obese or diabetic patients might help correct the metabolic defects and is viewed as an interesting therapeutic avenue. Brown fat cells are however not abundant in adults making their study and their therapeutic use difficult. Having access to an unlimited source of such cells would considerably accelerate the development of therapeutic approaches for metabolic diseases. During development of the embryo, brown fat forms from the same cells—a paraxial mesoderm (somitic) progenitor—that generate the skeletal muscles of the body (Billon and Dani, 2012). Described herein are protocols to differentiate skeletal muscle cells in vitro from mouse and human ES/iPS cells and are able to produce the common paraxial mesoderm (somitic) precursor to brown fat and muscle.

Lineage tracing and grafting experiments analysis during embryonic development showed that the dorsal Pax3$^+$ dermomyotome, which is shaped as an epithelial sheet, is multipotent and gives rise to the dermatome, the myotome and brown adipose (Buckingham, 2006; Atit et al., 2006; Seale et al., 2008). In the anterior trunk, brown adipose tissue (BAT) origin can be traced back to Engrailed (En)$^+$; Myf5$^+$ dermomyotomal progenitors (Seale et al., 2009; Seale et al., 2007; Seale and Lazar, 2009). Presumptive Myf5$^+$ Brown adipoblasts, instead of undergoing further myogenesis, switch to an adipogenic program controlled by the transcription factors Prdm16, C/EBPb and Ebf2 (Kajimura et al., 2009; Seale et al., 2008; Wang et al., 2014). Furthermore, lineage tracing of Pax7+ progenitors showed that BAT comes from the early somitic Pax7$^+$ progenitors, as later on (after E12.5 embryonic of development in mouse), the remaining somitic Pax7$^+$ are essentially restricted to skeletal muscles (Lepper and Fan, 2010). In mice, BAT starts to morphologically individualize around E15.5 and is clearly identifiable at E18.5.

While many medically-relevant cell types, such as neurons or cardiomyocytes are now generated efficiently from pluripotent stem cells from healthy or diseased subjects, methods for generation of BAT have met with limited success. During embryogenesis, BAT and WAT have a clear distinct origin with BAT progenitors deriving from a Myf5/Pax3/Pax7-expressing population arising from the paraxial mesoderm (Atit et al., 2006; Seale et al., 2008; Lepper and Fan, 2010) while WAT derive from the lateral plate (Gesta et al, 2007, Chau et al 2014). Moreover, BAT differentiates earlier during embryogenesis whereas WAT is mostly formed postnatally. To better explore the therapeutic potential of BAT, there is a need for methods allowing efficient production of BAT in vitro. A few approaches to produce BAT cells in vitro from pluripotent cells have been described. Differentiation of ES/iPS to a general adipocytic fate has been reported nearly two decades ago (Dani et al., 1997). Treatment of pluripotent stem cells with a complex cytokine cocktails (Nishio and Saeki, 2014; Nishio et al., 2012) or formation of embryonic bodies (Yamamoto et al., 2003) were also shown to be able to produce BAT-like cells in vitro. Alternatively, direct conversion strategies have used the forced expression of key regulators of adipogenic and BAT differentiation programs such as Pparg2, Cebp and Prdm16 (Ahfeldt et al., 2012) or of Pax3 (Mohsen-Kanson et al., 2014) to produce BAT-like cells. However, the progenitors obtained by these methods are still poorly characterized and appear to be largely immature (Hafner and Dani, 2014). In vivo, phenotypically, BAT shares a number of general adipocytic markers with WAT, including PGC1 alpha/beta, Ppar gamma, C/ebp. Some markers are enriched in BAT versus WAT, including Ebf2 and Ewsr1. Furthermore, BAT uniquely expresses the following markers UCP1, Dio2, Cidea2 and FABP4. So far, no attempts to differentiate pluripotent stem cells such as ES or iPS cells into BAT by recapitulating the developmental history of this lineage have been described.

Methods of Generating BAT Progenitor Cells

The present disclosure provides methods for generating BAT cells, preferably human BAT cells, from progenitor cells, e.g., paraxial mesoderm (presomitic mesoderm) (PAM) cells. PAM cells exhibit characteristics of progenitor cells of the Paraxial Mesoderm. In one embodiment, the PAM cells are characterized by the following properties:

a) they express one, two, or all three of the biomarkers Pax3, Myf5, and optionally Pax7, which are characteristic of Paraxial mesoderm progenitor cells, and b) they are multipotent cells, capable of differentiating into at least brown adipose, endothelial, skeletal, dermis and muscle cell lineages in vivo and/or in vitro with the appropriate culture conditions Optionally, they may have long term self-renewal properties, e.g., they can be maintained in culture more than 6 months. The multipotency of the PAM cells can be tested in vitro, e.g., by in vitro differentiation into adipose, skeletal, dermal or muscle cell lineages using the protocols described below, and in particular in the Examples.

In some embodiments, the progenitor cells, e.g., paraxial mesoderm cells, are induced paraxial mesoderm (iPAM) cells, preferably derived from induced pluripotent stem (iPS) cells or embryonic stem (ES) cells, e.g., human pluripotent stem cells. Methods for obtaining and generating PAM cells are known in the art; see, e.g., WO2013030243 and Chal et al. 2015; Loh et al., Cell. 2016 Jul. 14; 166(2):451-67; Shelton et al., Stem Cell Reports. 2014 Sep. 9; 3(3): 516-529; Xi et al., Cell Rep. 2017 Feb. 7; 18(6): 1573-1585; Choi et al., Cell Rep. 2016 Jun. 7; 15(10):2301-12; and Hosoyama et al., Stem Cells Transl Med. 2014 May; 3(5):564-74.

In some embodiments, the methods include culturing iPS or ES cells in the presence of one a Wnt activator, e.g., a Wnt ligand, GSK3beta inhibitor, or member of the R-spondin family, or of both a Wnt activator and a BMP inhibitor, e.g., an ALK inhibitor.

In some embodiments, progenitor cells isolated from a subject, e.g., autologous or primary cells, are differentiated using the described media; methods for isolating CD34$^+$ BAT progenitor cells from the skeletal muscle of a subject are described in US PG Pub 20160303100.

Wnt Activators

The present methods can include the use of agonists or activators of the canonical Wnt/beta catenin signaling pathway, characterized by a Wnt dependant inhibition of glycogen synthase kinase 3β (GSK-3β), leading to a subsequent stabilization of β-catenin, which then translocates to the nucleus to act as a transcription factor. As used herein the term "activator" denotes a molecule, e.g., antibody, protein, nucleic acid, or small molecule that enhances Wnt signaling activity. For example, for the canonical Wnt/β-catenin signaling pathway, this activity can be measured by Wnt reporter activity using established multimers of LEF/TCF binding sites reporters, and/or inhibition of GSK-3β, and/or activation of canonical Wnt target genes such as T, Tbx6, Msgn1, or Axin2.

Inhibitors of GSK-3β are known in the art and include lithium chloride (LiCl), Purvalanol A, olomoucine, alsterpaullone, kenpaullone, SB216763 (3-(2,4-dichlorophenyl)-4-(1-methyl-1H-indol-3-yl)-1H-pyrrole-2,5-dione) and SB415286 (3-[(3-chloro-4-hydroxyphenyl)amino]-4-(2-nitrophenyl)-1H-pyrrole-2,5-dio-ne) which are maleimide derivatives, benzyl-2-methyl-1,2,4-thiadiazolidine-3,5-dione (TDZD-8), 2-thio(3-iodobenzyl)-5-(1-pyridyl)-[1,3,4]-oxadiazole (GSK3 inhibitor II), 2,4-dibenzyl-5-oxothiadiazolidine-3-thione (OTDZT), (2'Z,3'E)-6-Bromoindirubin-3'-oxime (BIO), α 4 Dibromoacetophenone (i.e., Tau Protein Kinase I (TPK I) Inhibitor), 2-Chloro-1-(4,5-dibromo-thiophen-2-yl)-ethanone, N-(4-Methoxybenzyl)-N'-(5-nitro-1,3-thiazol-2-yl)urea (AR-A014418), and indirubins (e.g., indirubin-5-sulfonamide; indirubin-5-sulfonic acid (2-hydroxyethyl)-amide indirubin-3'-monoxime; 5-iodo-indirubin-3'-monoxime; 5-fluoroindirubin; 5,5'-dibromoindirubin; 5-nitroindirubin; 5-chloroindirubin; 5-methylindirubin, 5 bromoindirubin), 4-Benzyl-2-methyl-1,2,4-thiadiazolidine-3,5-dione (TDZD-8), 2-thio(3-iodobenzyl)-5-(1-pyridyl)-[1, 3,4]-oxadiazole (GSK3 inhibitor II), 2,4-Dibenzyl-5-oxothiadiazolidine-3-thione (OTDZT), (2'Z,3'E)-6-Bromoindirubin-3'-oxime (BIO), α 4 Dibromoacetophenone (i.e., Tau Protein Kinase I (TPK I) Inhibitor), 2-Chloro-1-(4,5-dibromo-thiophen-2-yl)-ethanone, (vi) N-(4-Methoxybenzyl)-N'-(5-nitro-1,3-thiazol-2-yl)urea (AR-A014418), and H-KEAPPAPPQSpP-NH2 (L803) or its cell-permeable derivative Myr-N-GKEAPPAPPQSpP-NH2 (L803-mts). Other GSK3β inhibitors are disclosed in U.S. Pat. Nos. 6,417,185; 6,489,344; 6,608,063 and Published U.S. Applications Nos. 20160375006 2; 0040138273; 20040106574; 20040077707; 20040034037; 20030216574; and 20030130289.

Other activators of Wnt signaling include WAY-316606 (SFRP Inhibitor) Bodine et al., Bone. 2009 June; 44(6): 1063-8; (hetero)arylpyrimidines (Gilbert et al., Bioorg Med Chem Lett. 2010 Jan. 1; 20(1):366-70); IQ1 (PP2A Activator) Miyabayashi et al., Proc Natl Acad Sci USA. 2007 Mar. 27; 104(13):5668-73 (2007); QS11 (ARFGAP1 Activator) Zhang et al., Proc Natl Acad Sci USA. 2007 May 1; 104(18):7444-8; SB-216763 (GSK3 Inhibitor) Coghlan et al., Chem Biol. 2000 October; 7(10):793-803 (2000); CHIR99021 (6-[[2-[[4-(2,4-Dichlorophenyl)-5-(5-methyl-1H-imidazol-2-yl)-2-pyrimidinyl]amino]ethyl]amino]-3-pyridinecarbonitrile, GSK3 Inhibitor); DCA (beta-catenin Activator) Pai et al., Mol Biol Cell. 2004 May; 15(5):2156-63; and 2-amino-4-[3,4-(methylenedioxy) benzyl-amino]-6-(3-methoxyphenyl) pyrimidine (AMBMP) Liu et al., Inflamm Res. 2016 January; 65(1):61-9.

Wnt ligands in natural or modified forms can also be used as Wnt activator in the form of purified or recombinant proteins. Wnt ligands comprise a large family of Wnt activators including but not limited to Wnt1, Wnt 3, Wnt 3a, Wnt 4, Wnt 5a, Wnt 7a, Wnt 8, Wnt 11 and Wnt 16. The R-spondins family encompassing R-spondin1 to 4 are potent Wnt signaling enhancer through their binding to LGR4/5 surface receptors. Natural or modified, synthetic, polypeptides fragments generated from known Wnt activator polypeptide sequence can also be potential Wnt activators. When the activator of the Wnt signaling pathway is a protein, it may be a purified protein or a recombinant protein or a synthetic protein. Alternatively, conditioned media produced from a cell line engineered to express one or several Wnt ligands can be used as a Wnt activator. Wnt signaling can also be activated by blocking negative regulators of Wnt signaling, such as Axin and APC using RNA interference.

BMP Inhibitors

A bone morphogenetic protein (BMP) antagonist or inhibitor refers to a molecule, e.g., antibodies, proteins, nucleic acids, or small molecules, that inhibits or attenuates the biological activity of the BMP signaling pathway either by directly interacting with BMP or by acting on components of the biological pathway in which BMP participates, such as a BMP receptor protein (e.g. BMP type I receptors ALK2 and/or ALK3) or downstream SMAD proteins). Typically, a compound is deemed to be an inhibitor of the BMP signaling pathway if, after culturing cells in the presence of said compound, the level of phosphorylated Smad 1, 5 or 8 is decreased compared to cells cultured in the absence of said compound. Levels of phosphorylated Smad proteins can be measured by Western blot using antibodies specific for the phosphorylated form of said Smad proteins.

Examples include noggin, an inhibitor of the transduction activity of the BMP type I receptors ALK2 and/or ALK3, chordin, or LDN193189, a dorsomorphin derivatives. Noggin, chordin, follistatin and gremlin block BMP signaling by sequestrating secreted BMP, preventing its binding to the receptor. The inhibitor of the BMP signaling pathway may be a BMP antagonist, a chemical compound that blocks BMP type I and/or type II receptors activity (BMP type I/II receptor inhibitor), an inhibitor of BMP type I and/or type II gene expression, or a molecule which inhibits any downstream step of the BMP signaling pathway. The inhibitor of BMP signaling may be a natural or a synthetic compound. When the inhibitor of the BMP signaling pathway is a protein, it may be a purified protein or a recombinant protein or a synthetic protein.

It is well known in the art that an inhibitor of BMP type I receptors may block the BMP signaling pathway, see for example Yu et al, Nat Chem Biol. 2008.

In a preferred embodiment, the inhibitor of BMP type I receptors is Dorsomorphin, a chemical compound or any derivatives generated by structure-activity studies [Cuny G D et al., 2008]. Dorsomorphin (6-[4-(2-Piperidin-1-yl-ethoxy)phenyl]-3-pyridin-4-yl-pyrazolo[1,5-a]pyrimidine, also known as Compound C, specifically inhibits BMP type I receptors (ALK2, 3, and 6) [Yu P B et al., 2008]. For additional BMP inhibitors, see WO2013030243.

Methods for Generating Induced BAT Cells

Methods for generating BAT cells from Pax3+ PAM/progenitor cells as described herein can include the use of either of two methods, as shown in FIG. 1. In the first method, referred to as HIFL-HI, Pax3+ cells are exposed to a serum-containing or serum-free medium containing HGF and IGF (e.g., DK15-HI) but lacking FGF; for example, after culture in a DMEM-based medium further containing 0.1 to 20% (e.g., 10-15%) KSR; 0.1 to 10% (e.g., 3-7% or about 5%) BSA and supplemented with 0.001 to 2 µg/ml (e.g., 0.001-0.1 µg/ml or about 0.01 µg/ml) HGF, 0.0001 to 2 µg/ml (e.g., 0.0001-0.1 µg/ml or about 0.002 µg/ml) IGF-1, 0.0001 to 2 µg/ml (e.g., 0.0001-0.1 µg/ml or about 0.002 µg/ml) FGF-2 (Peprotech, R&D Biosystems) and 0.01 to 100 µM (e.g., 0.01-5004 or about 0.1 µM) LDN193189 (HIFL medium) for 2 days.

This step corresponds to exposing the culture to a serum-containing or serum-free medium with or without the addition of at least one Hepatocyte Growth factor signaling pathway agonist/activator, one Insulin-like Growth factor signaling pathway agonist/activator, one Fibroblast Growth factor signaling pathway agonist/activator and/or one Bone Morphogenetic Protein signaling pathway antagonist/inhibitor for 1 to 4 days typically. The serum-free media can include a serum replacement supplement, for example a lipid-rich albumin such as the commercially available Knock-out serum replacement (Gibco™ KnockOut™ Serum Replacement (KnockOut™ SR)) (K, 1% to 15%), or as described in Garcia-Gonzalo and Bermonte, PLoS ONE. 2008; 3(1): e1384. In some embodiments, the serum replacement includes Amino Acids: Glycine, L-histidine, L-isoleucine, L-methionine, L-phenylalanine, L-proline, L-hydroxyproline, L-serine, L-threonine, L-tryptophan, L-tyrosine, L-valine; Vitamins/Antioxidants: Thiamine, reduced glutathione, ascorbic acid 2-PO4: trace elements: Ag+, Al3+, Ba2+, Cd2+, Co2+, Cr3+, Ge4+, Se4+, Br—, I—, F—, Mn2+, Si4+, V5+, Mo6+, Ni2+, Rb+, Sn2+, and Zr4+; and Proteins; Transferrin (iron-saturated), insulin, lipid-rich albumin (AlbuMAX™). See also Lee et al., Fertility and Sterility 86(4 Supp):1137-1145 (2006).

A Hepatocyte Growth factor signaling pathway agonist/activator is a molecule e.g., antibody, protein, nucleic acid, or small molecule, that enhances HGF signaling activity. Typically, a HGF signaling pathway agonist/activator binds to or directly activate the c-Met proto-oncogene (HGFR) receptor. Examples of known HGF signaling activators include Hepatocyte Growth Factor-Scatter Factor (HGF-SF), HGF variants such as described further in U.S. Pat. Nos. 5,227,158; 5,316,921 and 5,328,837; HGFR activating antibodies such as MAb DO-24, 6E10 or 3D6 described in Pietronave et al, Am J Physiol Heart Circ Physiol. 2010 April; 298(4):H1155-65 and U.S. patent Ser. No. 08/884,669. Among the intracellular signaling pathways transduced by HGFR activation are MAPK, STAT3, and PI3K/Akt signaling axis. These intracellular pathways activity can be monitored using biochemical reporter assays and for transduction cascade activation, known in the art. HGF signaling activity can be measured by biological assays such as mitogenic, motogenic or morphogenic activities as a result of HGF binding to a HGF receptor. In particular, c-MET activation lead to the disruption of cadherin-based cell-cell contacts, and promote cell motility as evidenced by a cell-scattering phenotype, which was first described with MDCK cells treated with HGF (Zhu et al., Cell Growth Differ. 1994 April; 5(4):359-66).

An Insulin-like Growth factor signaling pathway agonist/activator is a molecule e.g., antibody, protein, nucleic acid, or small molecule that enhances IGF signaling activity. Examples of known IGF activators include IGF-1 (e.g., somatomedin C), MGF, IGF-2 and Insulin, demethylasterriquinone B-1, (DMAQ-B1; Salituro et al, Recent Prog Horm Res. 2001; 56:107-26). Typically, an IGF signaling pathway agonist/activator binds to or directly activate IGF1 receptor (IGF1Ra, b), and/or the insulin receptor (IR), and/or Insulin receptor-related receptor IR-related receptor (IRR). IGF signaling transduction results in the activation of several intracellular pathways including RAS-MAP kinase pathway, PI3K/AKT, and PI3K/mTor signaling pathways. These intracellular pathways activity can be monitored using biochemical reporter assays and for transduction cascade activation, known in the art.

A Fibroblast Growth factor signaling pathway agonist/activator is a molecule e.g., antibody, protein, nucleic acid, or small molecule that enhances FGF signaling activity.

Examples of FGF signaling pathway agonist/activator are natural or recombinant proteins ligands including the 23 identified FGF ligands. FGF activators bind and/or activate one or several FGF receptors (FGFR1 to 4) leading to the activation of several signaling pathways including RAS-MAPK, PI3K-AKT, PLCγ and STAT signaling pathways.

These intracellular pathways activity can be monitored using biochemical reporter assays and for transduction cascade activation, known in the art.

Properties and examples of Bone Morphogenetic Protein signaling pathway antagonist/inhibitor have been described above.

Recombinant proteins and polypeptidic agonists or antagonists are typically supplemented each at 0.1 ng/mL to 1 mg/mL of culture medium. Small compounds/molecules activators or inhibitors are typically supplemented each at 1 nM to 1 mM. Afterwards, the medium was supplemented with only HGF and IGF-1 (HI medium).

In the second method, referred to as PRA-AdipoMix method, the Pax3$^+$ cells are exposed to a serum-containing or serum-free medium DMEM-based medium containing PD173074 (250 nM, Tocris) and Retinoic acid ([RA], 100 nM, Sigma) for 2-6 days. This step corresponds to exposing the culture to a serum-containing or serum-free medium with or without the addition of at least one Fibroblast Growth factor signaling pathway antagonist/inhibitor and/or a Retinoic signaling pathway agonist/activator for 1 to 6 days typically.

A Fibroblast Growth factor signaling pathway antagonist/inhibitor is a molecule e.g., antibody, protein, nucleic acid, or small molecule that inhibits or blocks FGF signaling activity. Examples of FGF signaling pathway antagonist/inhibitor include natural or recombinant proteins ligands including Sprouty 1, small molecules including SU5402, LY2874455, PD173074, SSR128129E (Dol-Gleizes et al, PLoS One. 2013 Nov. 4; 8(11):e80027). FGF antagonist/inhibitor bind and/or inhibit one or several FGF receptors (FGFR1 to 4) leading to the inhibition of several signaling pathways including RAS-MAPK, PI3K-AKT, PLCγ and STAT signaling pathways. These intracellular pathways activity can be monitored using biochemical reporter assays and for transduction cascade activation, known in the art.

A Retinoic acid signaling pathway agonist/activator is a molecule e.g., antibody, protein, nucleic acid, or small molecule that activates RA signaling pathway. Examples of retinoic signaling pathway agonist/activator are all-trans retinoic acid (RA); 9-cis RA; TTNPB; Tazarotene; AC 261066; AC 55649; Adapalene; AM 580; AM 80; BMS 753; BMS 961; CD 1530; CD 2314; CD 437; Ch 55; Isotretinoin; and TTNPB (4-[(E)-2-(5,6,7,8-Tetrahydro-5,5,8,8-tetramethyl-2-naphthalenyl)-1-propenyl]benzoic acid). Retinoic signaling pathway agonist/activator binds or directly activate one or several of the Retinoic acid receptors (RARα, β and γ). Transduction relies on heterodimerization of RAR with RXR and direct binding of DNA at retinoic acid response elements (RAREs) sites. Retinoic signaling pathway activity can be monitored using biochemical reporter assays, including RARE-LacZ system which expresses beta-galactosidase under the control of the retinoic acid responsive element, or activation of target genes such as the one listed in Freemantle et al, Oncogene. 2002 Apr. 25; 21(18): 2880-9), Savory et al, Dev Biol. 2014 Nov. 15; 395(2):199-208; and Balmer and Blomhoff, J Lipid Res. 2002 November; 43(11):1773-808. These intracellular pathways activity can be monitored using biochemical reporter assays and for transduction cascade activation, known in the art.

Recombinant proteins and polypeptidic agonists or antagonists are typically supplemented each at 0.1 ng/mL to 1 mg/mL of culture medium. Small compounds/molecules activators or inhibitors are typically supplemented each at 1 nM to 1 mM. Then, cultures are changed to an Adipocyte differentiation medium (referred herein to Adipomix), and refreshed every 2-3 days. Adipomix comprises a DMEM-based medium containing a serum replacement supplement as known in the art or described herein, 1× Insulin-Transferin-Selenium (ITS, Gibco) and further comprising 0.5 mM isobutylmethylxanthine (IBMX), 125 nM indomethacin (indometacin), 1 nM triiodothreonine (T3), 5 mM dexamethasone, and 1 mM rosiglitazone (see also a related adipogenic cocktail described in Sharma et al, PO 2014 and US20150030662). This step corresponds to exposing the culture to a serum-containing or serum-free medium with or without the addition of at least one of the factor listed above for at least 4 days typically. Possible supplements to the base medium for this step are: an Insulin receptor agonist/activator, an iron-binding glycoprotein that is internalized through Transferrin receptor-mediated endocytosis, a cofactor for anti-oxidants reduction, a methylated xanthine derivative which acts both as a competitive non selective phosphodiesterase inhibitor and a non selective adenosine receptor antagonist; a non steroidal non selective inhibitor of the cyclooxygenase (COX1 and 2) and thus an inhibitor of prostaglandin production; a thyroid hormone receptor (TR-α1,α2, β1 and/or β2) agonist/activator; a synthetic cortisol derivative; a thiazolidinedione molecule binding to the peroxisome proliferator-activated receptor gamma (PPARγ) nuclear receptor and acting as an Insulin sensitizer and an anti-inflammation compound.

These signaling pathways' activity can be monitored using biochemical reporter assays, e.g., for transduction cascade activation, known in the art.

Both methods trigger differentiation toward the brown adipocyte lineage. The induced BAT, or iBAT, is identifiable in culture by a characteristic morphology—large field of compact multilocular fat cells with a dark/brown contrast in brightfield or transmitted light imaging. iBAT can be specifically phenotyped with several BAT hallmarks, including the expression of the mitochondria uncoupling protein UCP1, nuclear compaction (note small, rounded nuclei), enrichment for mitochondria as labelled by MitoTracker™ dye, and lipid vesicle/loculi as labelled by Oil Red O. Additional marker genes include but are not limited to C/ebpβ, Prdm16, Pgc-1α, Ppar-α, Ebf2 and Thyroid receptor (TR) and also described in Basse et al, BMC Genomics 2015, 16:215. Additional physiological properties include but are not limited to cold-induced thermogenesis, metabolic activation by the PPAR activators Thiazolidinediones (ie. TZDs or glitazones), Natriuretic pepetides, Thyroid hormones, BMPs (e.g., Bmp7, 8b) and FGFs (e.g., Fgf 10, 21). Metabolic activation, such as higher energy consumption rate can be measured using metabolic platform assays such as Seahorse platform (Agilent).

Thiazolidinediones (ie. TZDs or glitazones), Natriuretic peptides, Thyroid hormones, BMPs (e.g., Bmp7, 8b) and FGFs (e.g., Fgf 10, 21). Metabolic activation, such as higher energy consumption rate can be measured using metabolic platform assays such as Seahorse platform (Agilent).

In general, the methods will produce a population of cells that is about 5-80% cells having the above characteristics.

In some embodiments, the cell culture medium does not contain any of the following: PPARγ activator, modulator or inhibitor; a PPARα activator or modulator; a PPARδ activator or modulator; a dual PPARα and PPARδ activator or modulator; a pan-PPAR (α, δ, γ) activator or modulator; a PDE4 inhibitor; a PDE7 inhibitor; a NRIP1 (RIP140) inhibitor, a PTEN inhibitor; an α1-adrenergic full or partial agonist; an RXRα activator or modulator; a PGC-1α activator; a PGC-1β inhibitor or activator; adiponectin or an activator of adiponectin receptor AdipoR1 and/or AdipoR2; an NOS inhibitor or activator; a Rho kinase-ROCK inhibitor; BDNF; a monoamine oxidase (MAO) A inhibitor and/or a MAO B inhibitor; an activator of SRC, an inhibitor of EGFR; an inhibitor of FAAH; an inhibitor of MAPK 1 or 2 or 4 or 5 or 7 or 8; an inhibitor of CDK9; a TGR5 agonist; an AMPK activator; BMP-7, an mTOR inhibitor; or an adenylate cyclase activator.

The methods can also include culturing the iBAT to increase the number of cells prior to use, or enriching or isolating the iBAT cells prior to use, e.g., using flow cytometry and magnetic-based sorting, based on cell surface markers that can include PDGFRα, VEGFR2, NPR, β3-AR, OxR1, BMPRII, Alk7 (Acvr1c), FGFR, and/or Irisin receptor.

Furthermore, BAT progenitors (brown adipoblasts) can also be isolated or purified using positive or negative surface markers typically used to identify multipotent mesenchymal progenitors and/or mesenchymal stem cells (MSCs). These include CD73 (5-Nucleotidase), CD90 (Thy1), CD105 (Endoglin), CD29 (See Xue et al, Nat Med. 2015 July; 21(7): 760-8), CD31, CD34, CD45 and CD56 (NCAM-1).

Methods of Using Induced BAT Cells

The iBAT cells produced using a method described herein can be used in a number of different ways. For example, the cells can be used in a transplantation protocol in which BAT cells are transplanted into a subject to treat metabolic disorders such as diabetes, insulin-resistance, obesity, hypertension, an insulin resistance disorder, or hepatic steatosis. The cells can optionally be derived from iPS cells or PAM cells obtained from the subject themselves (e.g., autologous), or can be allogeneic. The iBAT cells can be transplanted into areas where BAT is already present, e.g., a supraclavicular region, the nape of the neck, over the scapula, alongside the spinal cord, near proximal branches of the sympathetic nervous system that terminate in BAT depots, around at least one of the kidneys, the renal capsule, the liver, the skin, or elsewhere. The iBAT cells can be suspended in a suitable transplant media, such as phosphate buffered saline or other salines. The cell transplant mixture can be injected via a syringe with a needle ranging from 30 to 18 gauge, with the gauge of the needle being dependent upon such factors as the overall viscosity of the adipocyte suspension, into a target location. Preferably, needles ranging from 22 to 18 gauge and 30 to 27 gauge can be used. See, e.g., US20170000827; Liu et al., Cell Res 23, 851-854 (2013); and US20170014455. In some embodiments, the cells are present in a biocompatible semisolid or gel matrix, e.g., a hydrogel matrix, suitable for transplantation; for example, a hyaluronic acid-based hydrogel (see Tharp et al., Diabetes. 2015 November; 64(11):3713-24); Tharp and Stahl, Front Endocrinol (Lausanne). 2015; 6: 164; Vaicik et al., J. Mater. Chem. B, 2015, 3, 7903-7911); collagen/alginate microspheres (Yao et al., Biofabrication, 4(4): 045003 (2012)); or adipose tissue derived soluble extracellular matrix (sECM) and methylcellulose (MC) (see Kim et al., PLoS ONE 11(10): e0165265) can be used. See also Cho et al., Cell Transplat 16(4):421-434 (2007). Compositions comprising these hydrogels and the iBAT cells described herein are also within the scope of the present disclosure.

Methods of Screening (Test Compounds)

In addition to their use in transplantation, the iBAT cells derived using the present methods can also be used, e.g., for in vitro screening of drugs to determine their effect on BAT, including thermogenic assays. Thus, included herein are methods for screening test compounds, e.g., polypeptides, polynucleotides, inorganic or organic large or small molecule test compounds, to identify agents useful in the treatment of metabolic disorders such as diabetes, insulin-resistance, obesity, hypertension, an insulin resistance disorder, or hepatic steatosis. The methods can be used to identify whether a test compound has an effect on BAT, e.g., to increase BAT numbers or activity, or to decrease BAT numbers or activity.

As used herein, "small molecules" refers to small organic or inorganic molecules of molecular weight below about 3,000 Daltons. In general, small molecules useful for the invention have a molecular weight of less than 3,000 Daltons (Da). The small molecules can be, e.g., from at least about 100 Da to about 3,000 Da (e.g., between about 100 to about 3,000 Da, about 100 to about 2500 Da, about 100 to about 2,000 Da, about 100 to about 1,750 Da, about 100 to about 1,500 Da, about 100 to about 1,250 Da, about 100 to about 1,000 Da, about 100 to about 750 Da, about 100 to about 500 Da, about 200 to about 1500, about 500 to about 1000, about 300 to about 1000 Da, or about 100 to about 250 Da).

The test compounds can be, e.g., natural products or members of a combinatorial chemistry library. A set of diverse molecules should be used to cover a variety of functions such as charge, aromaticity, hydrogen bonding, flexibility, size, length of side chain, hydrophobicity, and rigidity. Combinatorial techniques suitable for synthesizing small molecules are known in the art, e.g., as exemplified by Obrecht and Villalgordo, *Solid-Supported Combinatorial and Parallel Synthesis of Small-Molecular-Weight Compound Libraries*, Pergamon-Elsevier Science Limited (1998), and include those such as the "split and pool" or "parallel" synthesis techniques, solid-phase and solution-phase techniques, and encoding techniques (see, for example, Czarnik, Curr. Opin. Chem. Bio. 1:60-6 (1997)). In addition, a number of small molecule libraries are commercially available. A number of suitable small molecule test compounds are listed in U.S. Pat. No. 6,503,713, incorporated herein by reference in its entirety.

Libraries screened using the methods of the present invention can comprise a variety of types of test compounds. A given library can comprise a set of structurally related or unrelated test compounds. In some embodiments, the test compounds are peptide or peptidomimetic molecules. In some embodiments, the test compounds are nucleic acids.

In some embodiments, the test compounds and libraries thereof can be obtained by systematically altering the structure of a first test compound, e.g., a first test compound that is structurally similar to a known natural binding partner of the target polypeptide, or a first small molecule identified as capable of binding the target polypeptide, e.g., using methods known in the art or the methods described herein, and correlating that structure to a resulting biological activity, e.g., a structure-activity relationship study. As one of skill in the art will appreciate, there are a variety of standard methods for creating such a structure-activity relationship. Thus, in some instances, the work may be largely empirical, and in others, the three-dimensional structure of an endogenous polypeptide or portion thereof can be used as a starting point for the rational design of a small molecule compound or compounds. For example, in one embodiment, a general library of small molecules is screened, e.g., using the methods described herein.

In some embodiments, a test compound is applied to a test sample comprising a BAT cell or tissue obtained using a method described herein, and one or more effects of the test compound is evaluated. For example, the methods can evaluate the ability of the test compound to alter expression of one or more of UCP-1, Dio2, Cidea2, FABP4, C/ebp, Ebf2, and/or Prdm16, and/or proliferation of BAT progenitors, and/or fat storage evaluated for example by Oil Red O staining, and/or BAT thermogenic activity, and/or BAT metabolic activity, as evaluated by measure of glycolysis, mitochondrial respiration, lipid synthesis, beta-oxidation and mitochondrial uncoupling.

Methods for evaluating each of these effects are known in the art. For example, ability to modulate expression of a protein can be evaluated at the gene or protein level, e.g., using quantitative PCR or immunoassay methods. In some embodiments, high throughput methods, e.g., protein or gene chips as are known in the art (see, e.g., Ch. 12, Genomics, in Griffiths et al., Eds. *Modern genetic Analysis,* 1999, W. H. Freeman and Company; Ekins and Chu, Trends in Biotechnology, 1999, 17:217-218; MacBeath and Schreiber, Science 2000, 289(5485):1760-1763; Simpson, *Proteins and Proteomics: A Laboratory Manual,* Cold Spring Harbor Laboratory Press; 2002; Hardiman, *Microarrays Methods and Applications: Nuts & Bolts,* DNA Press, 2003), can be used to detect an effect on the BAT. Ability to modulate signaling via the VEGFR2, atrial natriuretic peptide receptor (NPR), beta3 adrenergic receptor (β3-AR), OxR1, BMPRII, Alk7 (Acvr1c), FGFR, and/or Irisin receptor signaling pathways can be evaluated, e.g., using genetically encoded reporter assays and/or using biochemical assays for known intracellular transduction pathways transduction including, p38, PKC, Pi3K, and phosphoSMADs (see, e.g., Tchivileva et al., Mol Immunol. 2009 July; 46(11-12): 2256-2266; Kumar et al., 1356(2):221-228, 1997; Moshinsky et al., J Biomol Screen. 2003 August; 8(4):447-52; Zilberberg et al., BMC Cell Biol. 2007; 8: 41; Logeart-Avramoglou et al., Anal Biochem. 2006 Feb. 1; 349(1):78-86].

Thermogenic assays can include exposing the cells to thermogenesis-inducing factors, including but not limited to a GPR120 activator (e.g., GW9508 (see Quesada-Lopez et al., Nat Commun. 2016 Nov. 17; 7:13479) or Berberine (see Zhang et al., Nat Commun. 2014 Nov. 25; 5:5493) or exposure to cold.

A test compound that has been screened by a method described herein and determined to increase expression of UCP-1, Dio2, Cidea2, FABP4, C/ebp, Ebf2, and/or Prdm16, and/or increase proliferation of BAT progenitors, and/or increase fat storage and lipolysis evaluated for example by Oil Red O staining, and/or increase BAT mitochondrial content, and/or increase BAT thermogenic activity, and/or increase BAT metabolic activity, can be considered a candidate compound for treating a metabolic disorder.

Alternatively, the methods can be used to identify compounds that decrease BAT activity, e.g., to encourage weight gain or to treat conditions associated with increased BAT activity, hypermetabolism, underweight or weight loss associated with chronic disease. A test compound that has been screened by a method described herein and determined to decrease expression of UCP-1, Dio2, Cidea2, FABP4, C/ebp, Ebf2, and/or Prdm16, and/or decrease proliferation of BAT progenitors, and/or decrease fat storage and lipolysis evaluated for example by Oil Red O staining, and/or decrease BAT mitochondrial content, and/or decrease BAT thermogenic activity, and/or decrease BAT metabolic activity, can be considered a candidate compound for treating a condition associated with increased BAT activity, hypermetabolism, underweight, or weight loss associated with chronic disease.

A candidate compound that has been screened, e.g., in an in vivo model of a disorder, e.g., a metabolic disorder such as diabetes, insulin-resistance, obesity, hypertension, an insulin resistance disorder, or hepatic steatosis, and determined to have a desirable effect on the disorder, e.g., on one or more symptoms of the disorder, can be considered a candidate therapeutic agent. Candidate therapeutic agents, once screened in a clinical setting, are therapeutic agents. Candidate compounds, candidate therapeutic agents, and therapeutic agents can be optionally optimized and/or derivatized, and formulated with physiologically acceptable excipients to form pharmaceutical compositions.

Test compounds identified as "hits" (e.g., test compounds that increase expression of UCP-1, increase proliferation of BAT, increase Oil Red O staining, or to increase expression of UCP-1, Dio2, Cidea2, FABP4, C/ebp, Ebf2, and/or Prdm16, and/or increase proliferation of BAT progenitors, and/or increase fat storage evaluated for example by Oil Red O staining, and/or increase BAT mitochondrial content, and/or increase BAT thermogenic activity, and/or increase BAT metabolic activity) in an iBAT screen can be selected and systematically altered, e.g., using rational design, to optimize binding affinity, avidity, specificity, or other parameter. Such optimization can also be screened for using the methods described herein. Thus, in one embodiment, the invention includes screening a first library of compounds using a method known in the art and/or described herein, identifying one or more hits in that library, subjecting those hits to systematic structural alteration to create a second library of compounds structurally related to the hit, and screening the second library using the methods described herein.

Test compounds identified as hits can be considered candidate therapeutic compounds, useful in treating metabolic disorder such as diabetes, insulin-resistance, obesity, hypertension, an insulin resistance disorder, or hepatic steatosis. A variety of techniques useful for determining the structures of "hits" can be used in the methods described herein, e.g., NMR, mass spectrometry, gas chromatography equipped with electron capture detectors, fluorescence and absorption spectroscopy. Thus, the invention also includes compounds identified as "hits" by the methods described herein, and methods for their administration and use in the treatment, prevention, or delay of development or progression of a disorder described herein.

Test compounds identified as candidate therapeutic compounds can be further screened by administration to an animal model of metabolic disorder such as diabetes, insulin-resistance, obesity, hypertension, an insulin resistance disorder, or hepatic steatosis, as described herein. The animal can be monitored for a change in the disorder, e.g., for an improvement in a parameter of the disorder, e.g., a parameter related to clinical outcome. In some embodiments, the parameter is weight, and an improvement would be weight loss. In some embodiments, the subject is a human, e.g., a human with obesity, and the parameter is weight loss. In some embodiments, the subject is a human with, or an animal model of, a metabolic disorder such as diabetes, insulin-resistance, hypertension, an insulin resistance disorder, or hepatic steatosis, and the parameter is improved blood glucose control, improved insulin sensitivity, improved blood pressure control or improved liver enzyme levels. In this context, "improved" means returned to or near normal levels.

EXAMPLES

The invention is further described in the following examples, which do not limit the scope of the invention described in the claims.

Experimental Procedure

The following materials and methods were used in the Examples set forth below.

Mouse ES Cell Culture Maintenance. Undifferentiated mouse embryonic stem cells were cultured on feeders of mitomycin-C inactivated mouse embryonic fibroblasts at 37° C. in 5% CO2. Maintenance medium was composed of DMEM supplemented with 15% fetal bovine serum (FBS, Millipore), penicillin, streptomycin, 2 mM 1-glutamine, 0.1 mM nonessential amino acids, 0.1% β-mercaptoethanol, 1,500 U/ml LIF and optionally with 2i inhibitors (CHIRON99021 at 3 uM) and (PD0325901 at luM, Stemgent). Cells were passaged by trypsinization with TrypLE™ (Invitrogen).

In Vitro Differentiation

1—Induced Paraxial Mesoderm (iPAM) Differentiation from ES/iPS.

Prior to differentiation, mouse pluripotent (embryonic) stem cells were passaged twice onto gelatin-coated, feeder-free culture plates. These cells were subsequently differentiated toward paraxial mesoderm (presomitic mesoderm) using a Wnt activator and a BMP inhibitor, essentially as described in WO2013030243 and Chal et al. 2015.

Briefly, ES cells were trypsinized and plated at various densities (about 30,000/cm2) on gelatin-coated, feeder-free, multi-well plates directly in serum-free N2B27 medium supplemented with 1% Knock-out Serum Replacement (KnockOut™ SR, Gibco™), 0.1% bovine serum albumin (Gibco) and BMP4 at 10 ng/ml (Peprotech) for 2 days. Cells were then changed to a DMEM-based medium, containing 15% total of Knock-out serum replacement (Gibco™) (KnockOut™ SR, 1% to 15%). supplemented with 0.5% DMSO (Sigma), 0.1 µM LDN193189 (from Tocris or Miltenyi Biotec/Stemgent), and with either recombinant 30 ng/ml Rspo3 (Peprotech or R&D Biosystems) or with 5 µM CHIRON99021 (Chir; Tocris or Stemgent), for 4 days. Alternatively, the medium also contained between 1-5% Fetal bovine serum. Differentiation experiments were performed 4 times independently in duplicates. The rational of this step is to generate a Pax3-positive presomitic and/or somitic populations corresponding to the pre/dermomyotomal progenitor from ES/iPS cells in vitro.

2—Differentiation of Anterior PSM/Dermomyotomal (Somitic) Pax3$^+$ Progenitors to Brown Adipoblasts Populations and their Subsequent Phenotypical Maturation into Brown Adipocytes.

The rationale behind developing several methods to induce differentiation of brown adipocytes is supported by the previous observation that in vivo BAT from different antero-posterior regions of the body has been reported to originate from different precursors. Additionally, gender dependent differential contribution is also observed (Sanchez-Gurmaches et al, 2014). Furthermore, anterior BAT originates essentially from the early somitic Pax3/7$^+$ population.

2-1 Method 1 (HIFL-HI Method)

At day 6, when cells differentiated according to the protocol described in Chal et al (2015), have reached an early Pax3-positive anterior PSM/dermomyotome stage, cultures are changed to a DMEM-based medium with 15% KSR; 0.1% BSA and supplemented with 10 ng/ml HGF, 2 ng/ml IGF-1, 20 ng/ml FGF-2 (Peprotech, R&D Biosystems) and 0.1 µM LDN193189 (HIFL medium) for 2 days. After day 8 of differentiation, the medium was supplemented with only HGF and IGF-1 (HI medium). Alternatively, the medium also contained between 1-5% Fetal bovine serum. We found that removing FGF after day 8 of differentiation was promoting brown adipocytes specification from the Pax3$^+$ paraxial mesoderm progenitor population. The medium was changed every other day. Long-term differentiation experiments were performed at least four times independently, on more than 3 different mouse ES cell lines.

2-2 Method 2 (PRA-AdipoMix Method)

At day 6, when cells differentiated according to the protocol described in Chal et al (2015), have reached an early Pax3-positive anterior PSM/dermomyotome stage, cultures are changed to a DMEM-based medium containing PD173074 (250 nM, Tocris) and Retinoic acid ([RA], 100 nM, Sigma) for 2-6 days. The rationale of this step was to activate retinoic acid signaling and inhibit FGF signaling in the Pax3+ progenitors to specify a brown adipoblast population. At day 8-10 of differentiation, cultures are changed to an Adipocyte differentiation medium (referred thereafter to Adipomix), and refreshed every 2-3 days. Adipomix was composed of a DMEM-based medium containing 15% Knock-out serum replacement (KnockOut™ SR), 1× Insulin-Transferin-Selenium (ITS, Gibco™) and further comprising 0.5 mM isobutylmethylxanthine (IBMX), 125 nM indomethacin, 1 nM triiodothreonine (T3), 5 mM dexamethasone, and 1 mM rosiglitazone, partially adapted from the Adipogenic cocktail (described in Sharma et al, PO 2014 and US20150030662). The rationale for this step is promoting the maturation of brown adipoblasts into adipocytes with phenotypical hallmarks of brown adipose tissue.

Cell Culture Characterization

1—Lipid Droplets Content Analysis-OilRedO Staining

Oil Red O stain solution was prepared fresh by dissolving 0.6% (w/v) Oil red O (Sigma) powder in Isopropanol 60%. Adherent cell cultures were fixed with PFA 4% for 1 h at 4 C, rinsed with MilliQ® H2O at Room temperature, followed by a wash with 60% (v/v) Isopropanol:H2O. Cultures were then incubated with the Oil Red O stain for 45 min at RT. Excess stain was washed away by extensive rinse with MilliQ® H2O, and cell cultures were immediately imaged.

2—Mitochondria Content Analysis—MitoTracker™ Staining

A stock solution of the cell-permeant MitoTracker™ Green FM (Molecular Probes) was prepared by resuspending to 1 mM in DMSO and it was stored at −20 C, according to manufacturer's recommendation. The staining solution was prepared by dilution to DMEM-based serum free medium supplemented with 15% Knock-out serum (KnockOut™ SR, Gibco™), to a final MitoTracker™ Green FM concentration of 50 nM.

Live cultures were stained by changing the culture media to prewarmed (37° C.) MitoTracker™ staining solution. Cultures were incubated 35 minutes and rinsed several times with prewarmed DMEM-based serum free medium, and imaged live immediately.

3—Brown Adipocytes Biomarkers Analysis—Immunohistochemistry

Adherent cell culture plates were fixed for 1 h in 4% formaldehyde at Room temperature. Cultures were rinsed three times in PBS, followed by an incubation with a blocking buffer composed of Tris-buffered saline (TBS) containing 1% FBS and 0.1% Triton X-100. Primary antibodies were then diluted in blocking buffer and incubated overnight at 4° C. The next day, cultures were washed three times with TBST (TBS supplemented with 0.5% Tween®-20) and incubated with secondary antibodies (1:500) and Hoechst or Dapi (5 µg/ml) in blocking buffer for at least 2 h. Cultures were rinsed three times with TBST and changed to PBS before analysis. Antibody used in this study was anti-UCP-1 (Abcam 10983).

4—Image Acquisition and Processing

Live or fixed brightfield and fluorescent images were acquired on a Evos® FL. Images were processed with Adobe Photoshop. Lipid droplets maximum diameter were measured in ImageJ and droplets sizes were approximated by the corresponding surface area (in µm2) according to a rectilinear parallel projection (of a disk of the measured diameter).

Primary Fat Tissue Collection and Culture

Interscapular BAT was collected from 1 to 2 weeks old mouse pups. Tissues were minced with a scalpel blade and replated on gelatinized 24-well plates in DMEM-based medium with 15% KSR (Gibco); 0.1% BSA and supplemented with 10 ng/ml HGF, 2 ng/ml IGF-1 or in the Adipomix media, as described in method 1 and method 2 respectively, and supplemented with ROCK inhibitor. After 2 days, cultures were changed to the same media without ROCK inhibitor. Media was subsequently changed every 2-3 days, for 10 days.

Example 1

The present example describes generating brown adipose tissue (iBAT) in vitro by directed differentiation of ES/iPS cells. The method was derived in part from method described by Chal et al (2015) and WO2013030243 to differentiate mouse and human ES/iPS first toward a pre-somitic mesoderm fate and then to the myogenic lineage. In this new method, we can divert Paraxial mesoderm progenitors induced from ES/iPS in vitro from skeletal muscle differentiation (Chal et al., 2015) to a brown adipose differentiation fate.

Figure 4C:
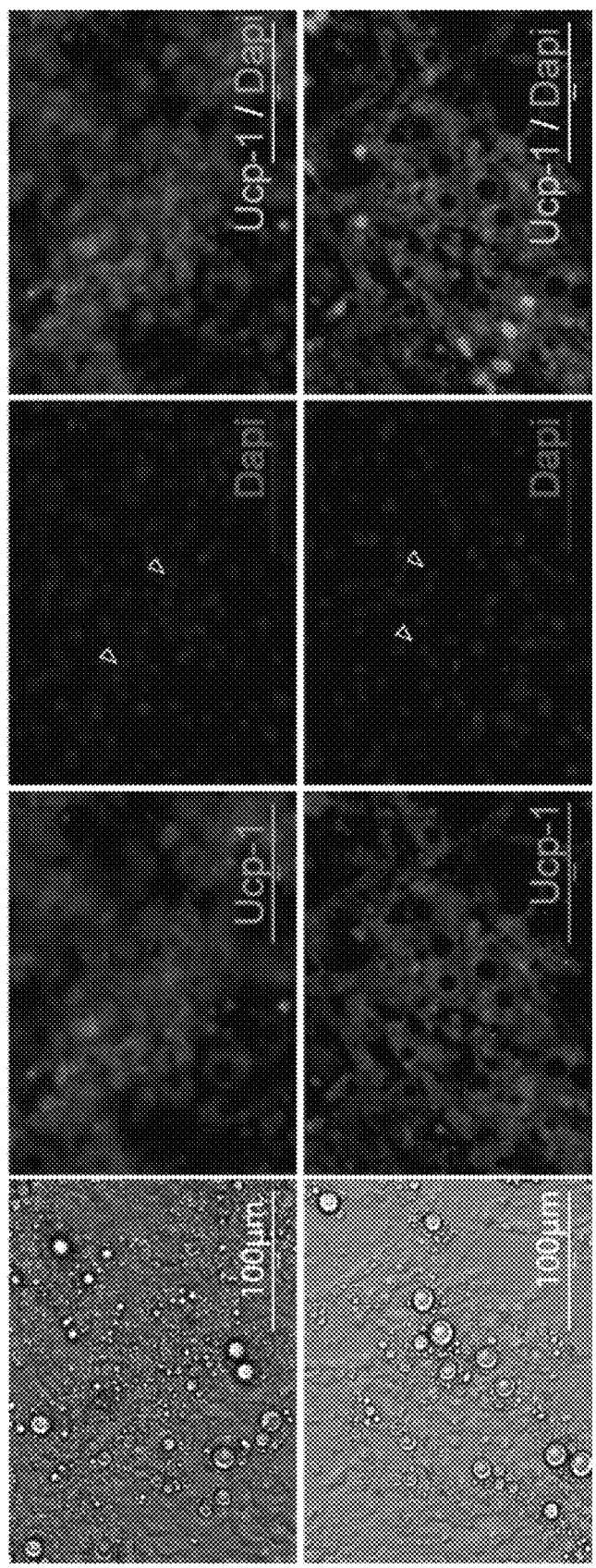
Figure 5:
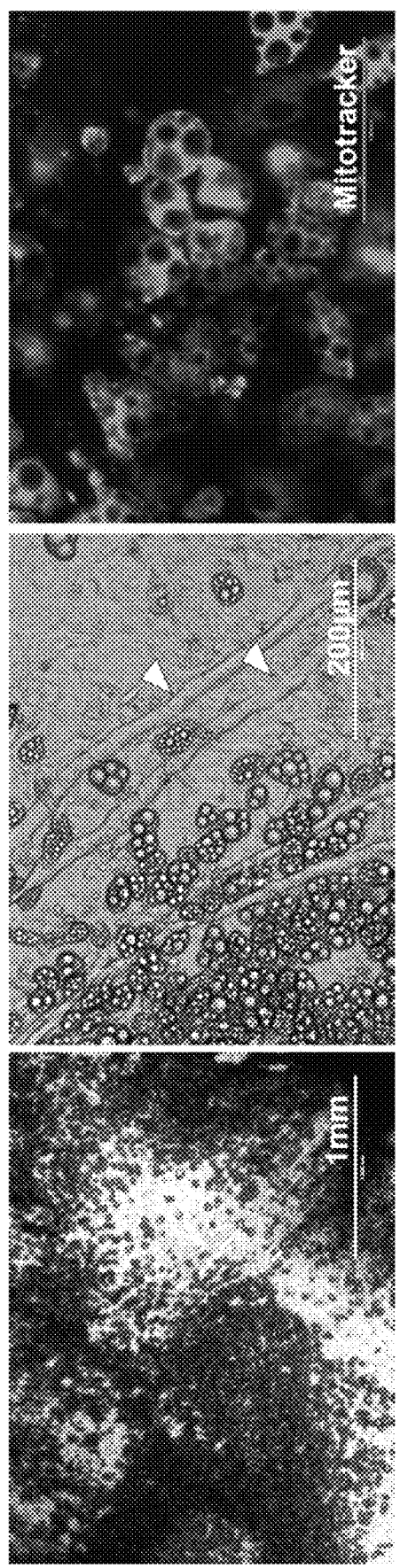
FIG. 5 shows adherent mESC cultures differentiated according to the Method 1 for 5 weeks (28 days). (left) Large fields of brown adipocytes covering most of the culture. (center) Higher resolution of left panel showing an example of co-differentiation of developmentally related cell linages: multilocular brown adipocytes and skeletal myofibers (arrowheads) can be generated from the same early Pax3+ paraxial mesoderm progenitors, suggesting the differentiation process recapitulates the embryonic development. (right) Higher resolution staining for mitochondria content using the MitoTracker™ dye (green, Thermo Fisher). The multilocular adipocytes generated in vitro from mouse ES cells are strongly positive for MitoTracker™, supporting their enrichment in mitochondria. Note the restriction of the MitoTracker™ positivity to the cell cytoplasm, excluding the lipids droplets.

We developed two methods that resulted in the differentiation of populations of iBAT in vitro. The brown adipocyte lineage derives from early Dermomyotomal (Pax3/7$^+$) progenitors of the paraxial mesoderm. These precursors differentiate in vitro after 6-8 days when ES/iPS cells are treated as described in Chal et al (2015) (FIG. 1). In method 1, exposure to a serum-free medium containing HGF and IGF (i.e., DK15-HI) but lacking FGF triggered their differentiation toward the brown adipocyte lineage in less than 2 weeks. Large fields of iBAT were identifiable in culture by their characteristic morphology: brown-colored fat cells exhibiting small lipid droplets (multilocular) as exemplified (FIG. 2-5). Lipid droplets size ranged from micron-up to hundreds of µm$^2$, depending of the differentiation stages and the cell populations. iBAT exhibited also several additional hallmarks of in vivo BAT, most notably expression of the mitochondria uncoupling protein UCP1 (FIG. 4), nuclear compaction (note small, rounded nuclei, at time centrally located) (FIG. 4), enrichment for mitochondria as labelled by mitotracker dye (FIG. 5). iBAT can also be found sometimes in close association to skeletal muscles, a cell type which shares the same developmental origin with BAT (FIG. 4).

Figure 6:
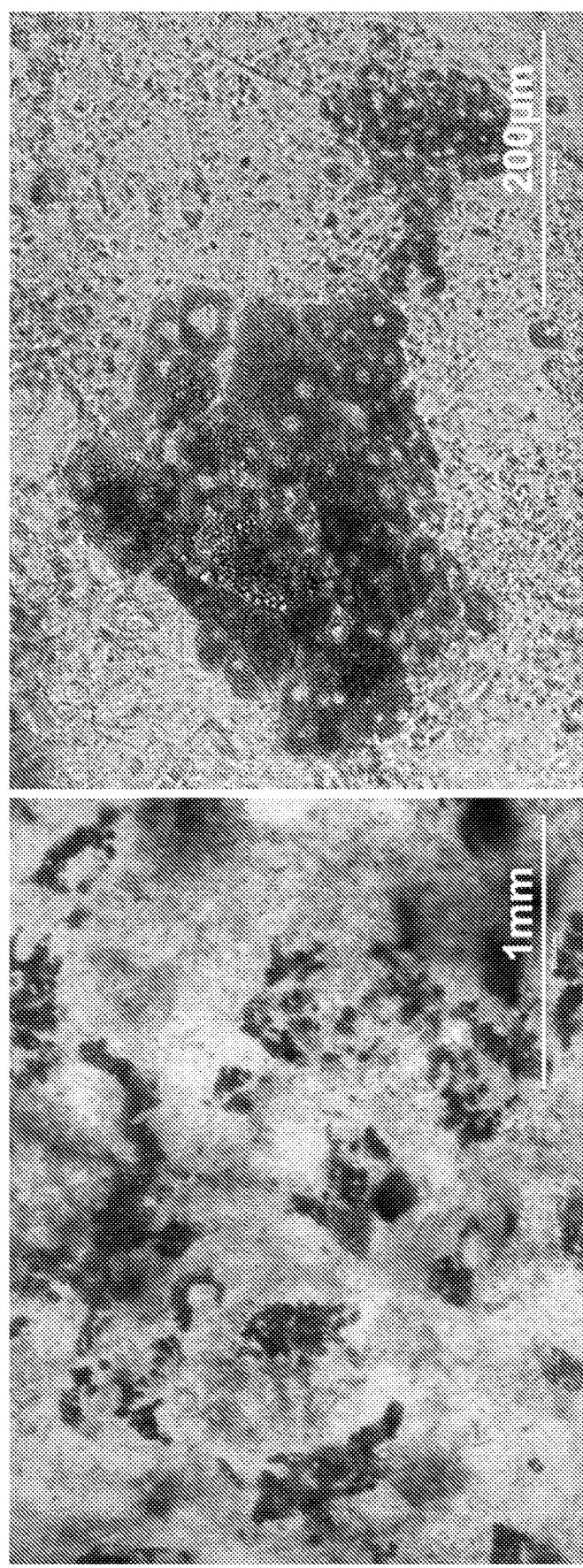
FIG. 6 shows large clusters of brown fat cells (adipoblasts, adipocytes) that can be detected at 4 weeks of differentiation (here at day 30 of differentiation) of mouse ES cells using Method 2. After paraxial mesoderm induction, mouse ES cultures were exposed to a DMEM-based serum-free medium containing Retinoic acid and the FGF inhibitor PD173074, followed by culture in the AdipoMix medium. (left) Brown adipose tissue forms as large group of dark brown-colored adipocytes which are tightly clustered. (right) Higher magnification of a BAT cluster showing the packed arrangement of multilocular cells exhibiting a high number of small lipid droplets and a circular and compacted nucleus in a central position, at times binucleated. Lipid droplets sizes ranged from 0.1 up to tens of $\mu m^2$ in surface area according to a rectilinear parallel projection.
Figure 7:
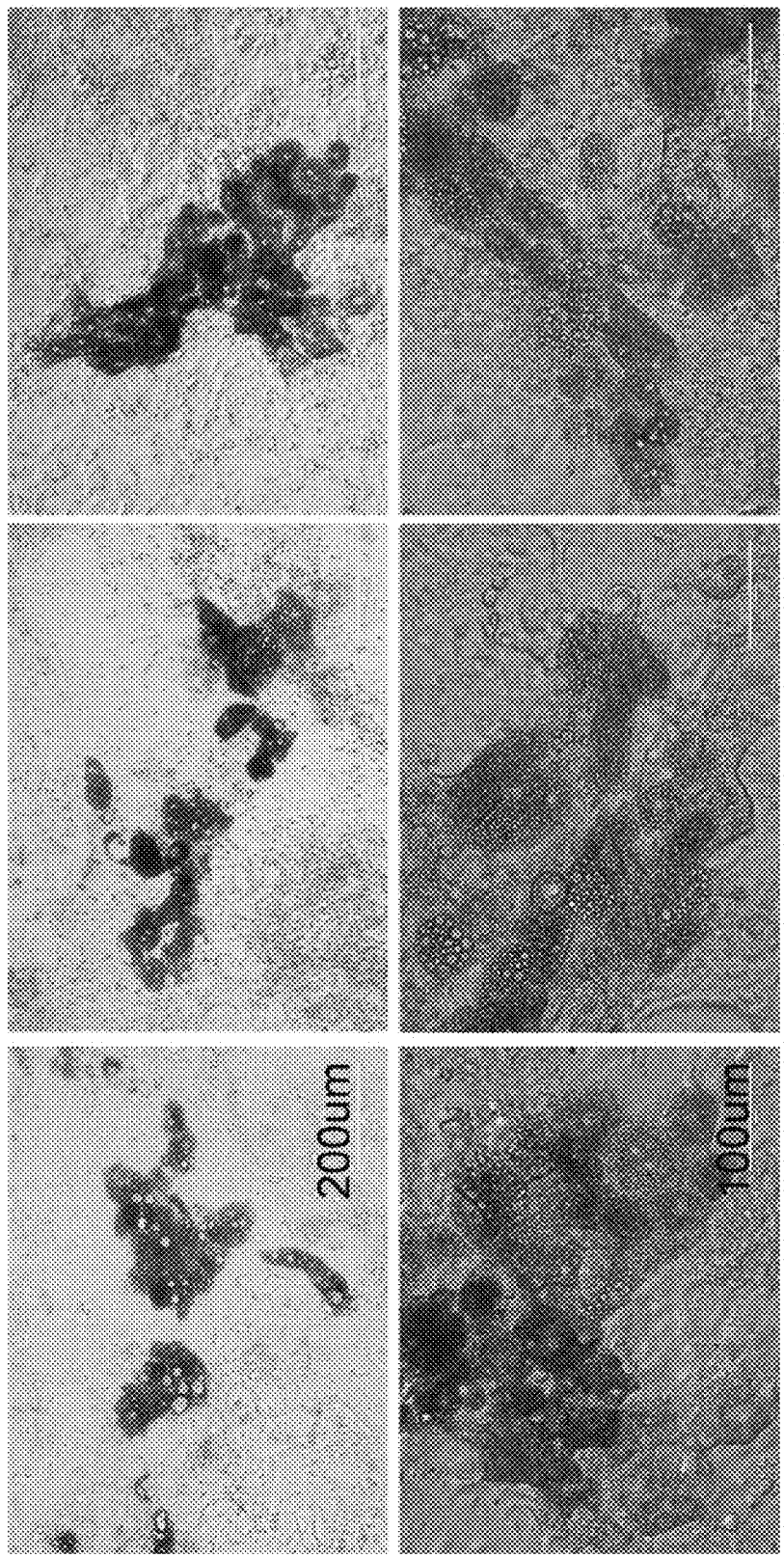
FIG. 7 shows individual clusters of brown multilocular adipocytes differentiated in vitro from mESCs with Method 2 after 55 days of culture. Note the tight packing of lipid droplets in the cells, the overall dark-brown coloration of the clusters, and the compacted nuclei in central position.
Figure 8:
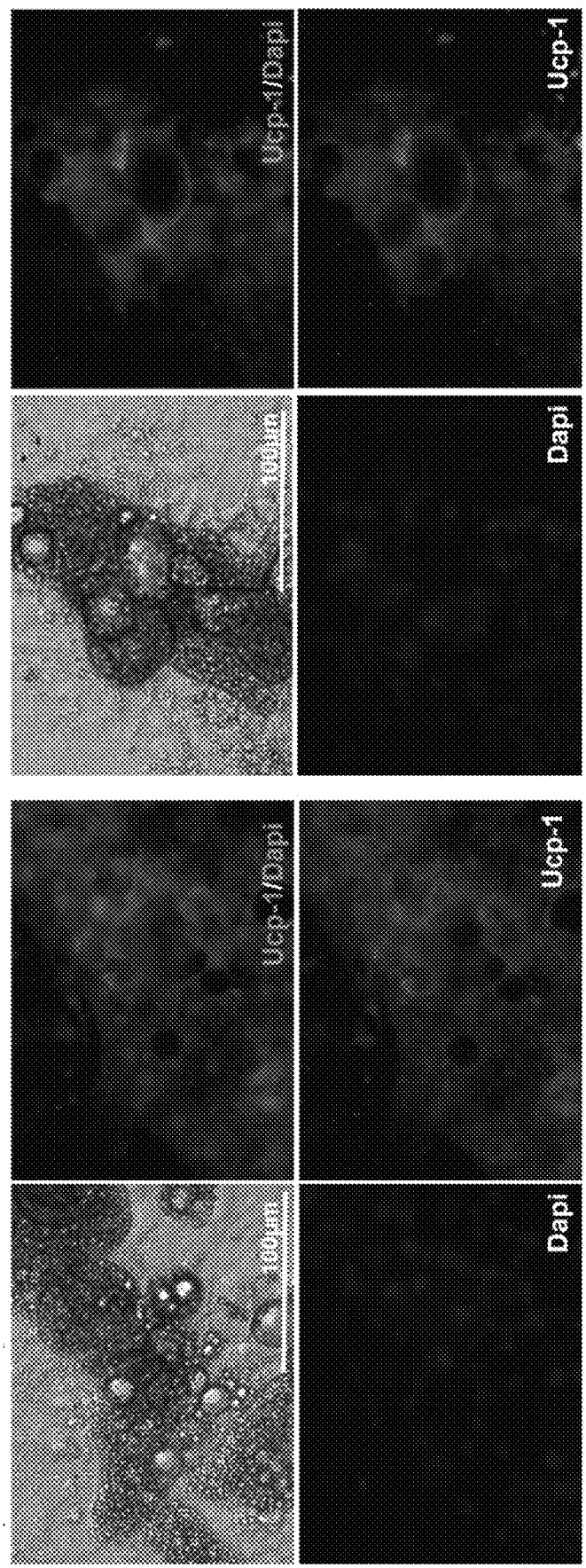
FIG. 8 shows clusters of brown fat cells (adipoblasts, adipocytes) at day 55 of differentiation of mouse ES cells using Method 2, stained with Ucp-1. Note that Ucp-1 staining is specific to cytoplasm.
Figure 9:
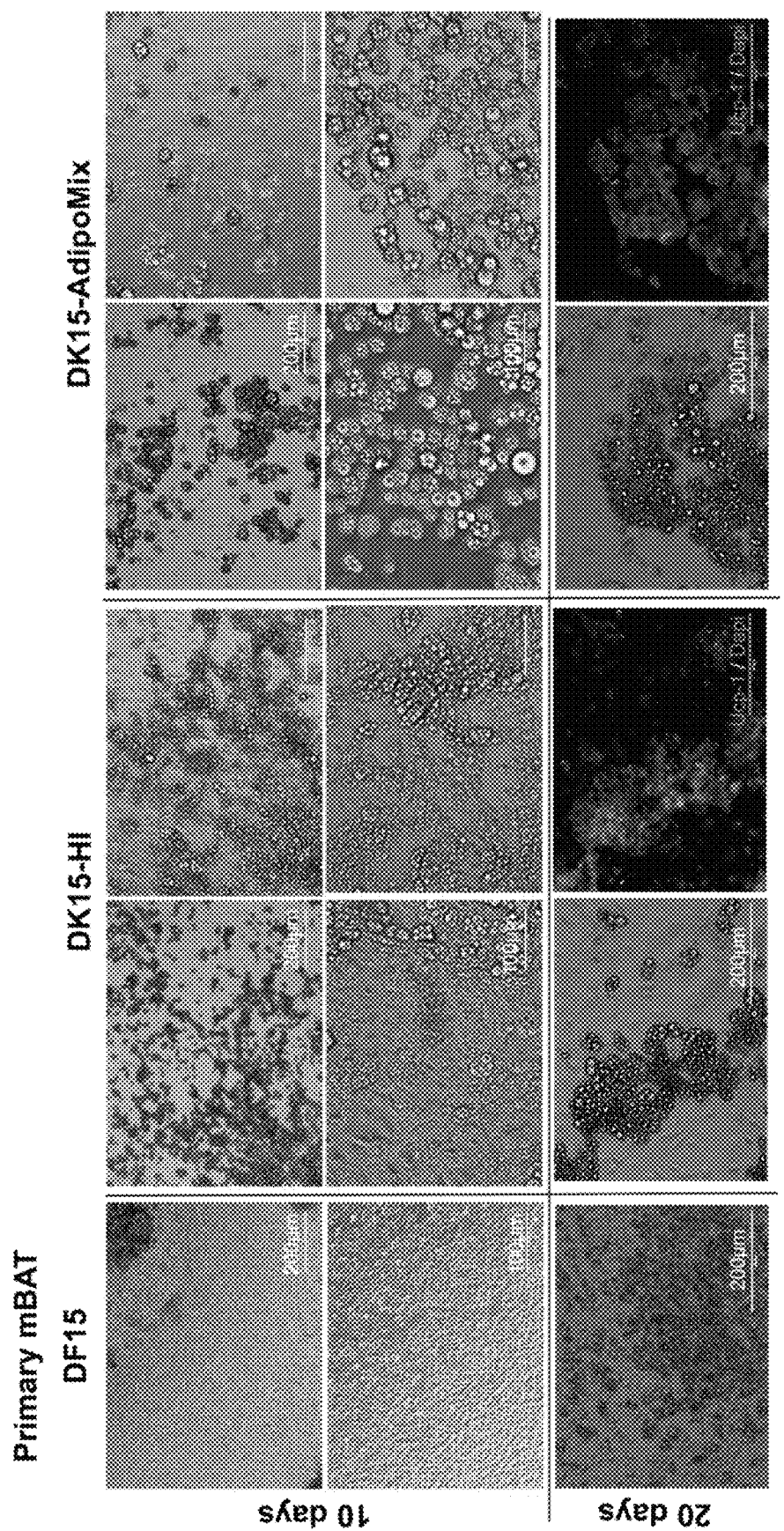
FIG. 9 shows a primary culture of mouse interscapular brown adipose tissue. A BAT biopsy was collected from pups at Postnatal day 10, minced and cultured for 10 days and 20 days on gelatin-coated plates, in the terminal DMEM-based (D) serum-free media of method 1 (HI) or method 2 (AdipoMix) supplemented with a serum-replacement supplement 15% KSR (K15), or alternatively in DMEM-based media containing 15% FBS (DF15) as a control. (left) Primary BAT cultured in 15% FBS remained mesenchymal-like with little recognizable, differentiated features. After 20 days of culture, adipocytes with limited differentiation and containing micrometer-size lipid droplets are visible. (center) Primary BAT cultured in method 1 terminal medium (DK15-HI) formed fields of brown adipose cells with multilocular feature. By 20 days, differentiated adipocytes contained numerous lipid droplets of various sizes (ranging from 1 $\mu m^2$ to tens of $\mu m^2$ in surface area according to a rectilinear parallel projection), had compact round nuclei and were positive for Ucp-1. This phenotype was very reminiscent of the cells obtained in vitro with method 1 from ES/iPS. (right) Primary BAT cultured in method 2 terminal medium (DK15-AdipoMix) formed groups of clustered brown adipose cells with multilocular lipid droplets, more limited in size distribution, had compact round nuclei, at time binucleated, and were positive for Ucp-1. This phenotype was also reminiscent of the cells obtained in vitro from ES/iPS with method 2. Altogether, this supports the idea that the cytological properties (phenotype) of primary and pluripotent stem cell-derived BAT cells can be modulated in vitro by culturing them in various media, including media described in Method 1 and Method 2 herein.

In method 2, exposure of ES/iPS cells to a medium containing retinoic acid (RA) and an FGF inhibitor for 2 to 6 days also triggers their differentiation toward the brown adipocyte lineage. Subsequent exposure to an adipocyte differentiation medium led to the formation of iBAT clusters distributed throughout the cultures as exemplified (FIGS. 6-8). iBAT clusters exhibited a granular cytoplasm containing tightly packed small lipid droplets (multilocular) within brown fat cells harboring a compact, round nucleus, located at time centrally and sometimes even binucleated, as reported in vivo (Napolitano and Fawcett, 1958). To validate the phenotype of the ES/iPS-derived BAT cells obtained in vitro, we cultured primary mouse BAT tissue in the media of method 1 or 2 described above. After 10 to 20 days in culture in HGF/IGF medium or the AdipoMix media, we observed the generation of fields and clusters of brown fat cells very reminiscent of the ones obtained from in vitro differentiation of ES/iPS (FIG. 9).

REFERENCES

Ahfeldt, T., Schinzel, R. T., Lee, Y. K., Hendrickson, D., Kaplan, A., Lum, D. H., Camahort, R., Xia, F., Shay, J., Rhee, E. P., et al. (2012). Programming human pluripotent stem cells into white and brown adipocytes. Nat Cell Biol 14, 209-219.

Atit, R., Sgaier, S. K., Mohamed, O. A., Taketo, M. M., Dufort, D., Joyner, A. L., Niswander, L. and Conlon, R. A. (2006). Beta-catenin activation is necessary and sufficient to specify the dorsal dermal fate in the mouse. Dev Biol 296, 164-176.

Barberi, T., Willis, L. M., Socci, N. D. and Studer, L. (2005). Derivation of multipotent mesenchymal precursors from human embryonic stem cells. PLoS medicine 2, e161.

Billon, N. and Dani, C. (2012). Developmental origins of the adipocyte lineage: new insights from genetics and genomics studies. Stem cell reviews 8, 55-66.

Boon, M. R., Nascimento, E. B. and van Marken Lichtenbelt, W. D. (2015). Tracing human brown fat. Nat Med 21, 667-668.

Borensztein, M., Viengchareun, S., Montarras, D., Journot, L., Binart, N., Lombes, M. and Dandolo, L. (2012). Double Myod and Igf2 inactivation promotes brown adipose tissue development by increasing Prdm16 expression. FASEB J 26, 4584-4591.

Buckingham, M. (2006). Myogenic progenitor cells and skeletal myogenesis in vertebrates. Curr Opin Genet Dev 16, 525-532.

Chal, J., Oginuma, M., Al Tanoury, Z., Gobert, B., Sumara, O., Hick, A., Bousson, F., Zidouni, Y., Mursch, C., Moncuquet, P., et al. (2015). Differentiation of pluripotent stem cells to muscle fiber to model Duchenne muscular dystrophy. Nat Biotechnol 33, 962-969.

Crisan, M., Casteilla, L., Lehr, L., Carmona, M., Paoloni-Giacobino, A., Yap, S., Sun, B., Leger, B., Logar, A., Penicaud, L., et al. (2008). A reservoir of brown adipocyte progenitors in human skeletal muscle. Stem Cells 26, 2425-2433.

Cristancho, A. G. and Lazar, M. A. (2011). Forming functional fat: a growing understanding of adipocyte differentiation. Nat Rev Mol Cell Biol 12, 722-734.

Dani, C., Smith, A. G., Dessolin, S., Leroy, P., Staccini, L., Villageois, P., Darimont, C. and Ailhaud, G. (1997). Differentiation of embryonic stem cells into adipocytes in vitro. J Cell Sci 110 (Pt 11), 1279-1285.

Doan-Xuan, Q. M., Sarvari, A. K., Fischer-Posovszky, P., Wabitsch, M., Balajthy, Z., Fesus, L. and Bacso, Z. (2013). High content analysis of differentiation and cell death in human adipocytes. Cytometry A 83, 933-943.

Fawcett, D. W. (1952). A comparison of the Histological Organization and cytochemical reactions of brown and white adipose tissues. Journal of morphology 90, 363-405.

Hadadeh, O., Barruet, E., Peiretti, F., Verdier, M., Bernot, D., Hadjal, Y., Yazidi, C. E., Robaglia-Schlupp, A., De Paula, A. M., Negre, D., et al. (2012). The plasminogen activation system modulates differently adipogenesis and myogenesis of embryonic stem cells. PLoS ONE 7, e49065.

Hafner, A. L., Contet, J., Ravaud, C., Yao, X., Villageois, P., Suknuntha, K., Annab, K., Peraldi, P., Binetruy, B., Slukvin, II, et al. (2016). Brown-like adipose progenitors derived from human induced pluripotent stem cells: Identification of critical pathways governing their adipogenic capacity. Sci Rep 6, 32490.

Hafner, A. L. and Dani, C. (2014). Human induced pluripotent stem cells: A new source for brown and white adipocytes. World journal of stem cells 6, 467-472.

Harms, M. and Seale, P. (2013). Brown and beige fat: development, function and therapeutic potential. Nat Med 19, 1252-1263.

Hwang, Y., Suk, S., Lin, S., Tierney, M., Du, B., Seo, T., Mitchell, A., Sacco, A. and Varghese, S. (2013). Directed in vitro myogenesis of human embryonic stem cells and their in vivo engraftment. PLoS ONE 8, e72023.

Kajimura, S., Seale, P., Kubota, K., Lunsford, E., Frangioni, J. V., Gygi, S. P. and Spiegelman, B. M. (2009). Initiation of myoblast to brown fat switch by a PRDM16-C/EBP-beta transcriptional complex. Nature 460, 1154-1158.

Kajimura, S., Seale, P. and Spiegelman, B. M. (2010). Transcriptional control of brown fat development. Cell Metab 11, 257-262.

Kazantzis, M., Takahashi, V., Hinkle, J., Kota, S., Zilberfarb, V., Issad, T., Abdelkarim, M., Chouchane, L. and Strosberg, A. D. (2012). PAZ6 cells constitute a representative model for human brown pre-adipocytes. Frontiers in endocrinology 3, 13.

Lee, H., Haller, C., Manneville, C., Doll, T., Fruh, I., Keller, C. G., Richards, S. M., Ibig-Rehm, Y., Patoor, M., Goette, M., et al. (2016). Identification of Small Molecules Which Induce Skeletal Muscle Differentiation in Embryonic Stem Cells via Activation of the Wnt and Inhibition of Smad2/3 and Sonic Hedgehog Pathways. Stem Cells 34, 299-310.

Liu, X., Wang, S., You, Y., Meng, M., Zheng, Z., Dong, M., Lin, J., Zhao, Q., Zhang, C., Yuan, X., et al. (2015). Brown Adipose Tissue Transplantation Reverses Obesity in Ob/Ob Mice. Endocrinology 156, 2461-2469.

Mahmood, A., Harkness, L., Schroder, H. D., Abdallah, B. M. and Kassem, M. (2010) Enhanced differentiation of human embryonic stem cells to mesenchymal progenitors by inhibition of TGF-beta/activin/nodal signaling using SB-431542. J Bone Miner Res 25, 1216-1233.

Mohsen-Kanson, T., Hafner, A. L., Wdziekonski, B., Takashima, Y., Villageois, P., Carriere, A., Svensson, M., Bagnis, C., Chignon-Sicard, B., Svensson, P. A., et al. (2014). Differentiation of human induced pluripotent stem cells into brown and white adipocytes: role of Pax3. Stem Cells 32, 1459-1467.

Napolitano, L. and Fawcett, D. (1958). The fine structure of brown adipose tissue in the newborn mouse and rat. The Journal of biophysical and biochemical cytology 4, 685-692.

Nishio, M. and Saeki, K. (2014). Differentiation of human pluripotent stem cells into highly functional classical brown adipocytes. Methods Enzymol 537, 177-197.

Nishio, M., Yoneshiro, T., Nakahara, M., Suzuki, S., Saeki, K., Hasegawa, M., Kawai, Y., Akutsu, H., Umezawa, A., Yasuda, K., et al. (2012). Production of functional classical brown adipocytes from human pluripotent stem cells using specific hemopoietin cocktail without gene transfer. Cell Metab 16, 394-406.

Rajakumari, S., Wu, J., Ishibashi, J., Lim, H. W., Giang, A. H., Won, K. J., Reed, R. R. and Seale, P. (2013). EBF2 determines and maintains brown adipocyte identity. Cell Metab 17, 562-574.

Sakurai, H., Era, T., Jakt, L. M., Okada, M., Nakai, S., Nishikawa, S. and Nishikawa, S. (2006). In vitro modeling of paraxial and lateral mesoderm differentiation reveals early reversibility. Stem Cells 24, 575-586.

Sakurai, H., Inami, Y., Tamamura, Y., Yoshikai, T., Sehara-Fujisawa, A. and Isobe, K. (2009). Bidirectional induction toward paraxial mesodermal derivatives from mouse ES cells in chemically defined medium. Stem Cell Res 3, 157-169.

Sakurai, H., Sakaguchi, Y., Shoji, E., Nishino, T., Maki, I., Sakai, H., Hanaoka, K., Kakizuka, A. and Sehara-Fujisawa, A. (2012). In vitro modeling of paraxial mesodermal progenitors derived from induced pluripotent stem cells. PLoS ONE 7, e47078.

Sanchez-Gurmaches, J. and Guertin, D. A. (2014a). Adipocyte lineages: tracing back the origins of fat. Biochim Biophys Acta 1842, 340-351.

Sanchez-Gurmaches, J. and Guertin, D. A. (2014b). Adipocytes arise from multiple lineages that are heterogeneously and dynamically distributed. Nature communications 5, 4099.

Seale, P., Bjork, B., Yang, W., Kajimura, S., Chin, S., Kuang, S., Scime, A., Devarakonda, S., Conroe, H. M., Erdjument-Bromage, H., et al. (2008). PRDM16 controls a brown fat/skeletal muscle switch. Nature 454, 961-967.

Seale, P., Kajimura, S. and Spiegelman, B. M. (2009). Transcriptional control of brown adipocyte development and physiological function—of mice and men. Genes Dev 23, 788-797.

Seale, P., Kajimura, S., Yang, W., Chin, S., Rohas, L. M., Uldry, M., Tavernier, G., Langin, D. and Spiegelman, B. M. (2007). Transcriptional control of brown fat determination by PRDM16. Cell Metab 6, 38-54.

Seale, P. and Lazar, M. A. (2009). Brown fat in humans: turning up the heat on obesity. Diabetes 58, 1482-1484.

Sharma, A., Huard, C., Vernochet, C., Ziemek, D., Knowlton, K. M., Tyminski, E., Paradis, T., Zhang, Y., Jones, J. E., von Schack, D., et al. (2014). Brown fat determination and development from muscle precursor cells by novel action of bone morphogenetic protein 6. PLoS ONE 9, e92608.

Timmons, J. A., Wennmalm, K., Larsson, O., Walden, T. B., Lassmann, T., Petrovic, N., Hamilton, D. L., Gimeno, R. E., Wahlestedt, C., Baar, K., et al. (2007). Myogenic gene expression signature establishes that brown and white adipocytes originate from distinct cell lineages. Proc Natl Acad Sci USA 104, 4401-4406.

Unser, A. M., Mooney, B., Con, D. T., Tseng, Y. H. and Xie, Y. (2016). 3D brown adipogenesis to create "Brown-Fat-in-Microstrands". Biomaterials 75, 123-134.

Villarroya, F. and Giralt, M. (2015). The Beneficial Effects of Brown Fat Transplantation: Further Evidence of an Endocrine Role of Brown Adipose Tissue. Endocrinology 156, 2368-2370.

Wang, W., Kissig, M., Rajakumari, S., Huang, L., Lim, H. W., Won, K. J. and Seale, P. (2014). Ebf2 is a selective marker of brown and beige adipogenic precursor cells. Proc Natl Acad Sci USA 111, 14466-14471.

Whittle, A. J., Lopez, M. and Vidal-Puig, A. (2011). Using brown adipose tissue to treat obesity—the central issue. Trends in molecular medicine 17, 405-411.

Xue, R., Lynes, M. D., Dreyfuss, J. M., Shamsi, F., Schulz, T. J., Zhang, H., Huang, T. L., Townsend, K. L., Li, Y., Takahashi, H., et al. (2015). Clonal analyses and gene profiling identify genetic biomarkers of the thermogenic potential of human brown and white preadipocytes. Nat Med 21, 760-768.

Yamamoto, M., Tachibana, T., Hashimoto, H., Ishiwata, I. and Ishikawa, H. (2003). The differentiation of early embryonic stem cells into adipocytes-like cells. Human cell 16, 117-122.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An in vitro method of generating an induced Brown Adipose Tissue (iBAT) cell, the method comprising:
    providing a paraxial mesoderm (PAM) cell that expresses at least one of pair box gene 3 (Pax3), myogenic factor 5 (Myf5), and pair box gene 7 (Pax7);
    culturing the PAM cell in conditions comprising:
    (i) medium comprising effective amounts of each of an hepatocyte growth factor (HGF) signaling pathway activator, an insulin-like growth factor (IGF) signaling pathway activator, a fibroblast growth factor (FGF) signaling pathway activator, and a bone morphogenetic (BMP) signaling pathway inhibitor for at least one day, followed by culturing in a medium comprising an HGF signaling pathway activator and an IGF signaling pathway activator but lacking a FGF signaling pathway activator; or
    (ii) medium comprising an FGF signaling pathway inhibitor and a Retinoic acid signaling pathway activator for two to six days, followed by an adipocyte differentiation medium;
    under conditions and for a time sufficient for the cells to differentiate into iBAT cells that express uncoupling protein 1 (UCP-1).

2. The method of claim 1, wherein the adipocyte differentiation medium comprises a serum replacement supplement; Insulin-Transferin-Selenium; isobutylmethylxanthine (IBMX); indomethacin, triiodothreonine (T3); dexamethasone; and rosiglitazone.

3. The method of claim 1, wherein the iBAT cell is a multilocular fat cell with a dark or brown coloration in brightfield imaging; adherent or in suspension; has circular compacted nuclei; is enriched for mitochondria; and is enriched in lipid droplets of various sizes ranging from 0.1 µm2 to 1000 µm2 in surface area according to a rectilinear parallel projection, or ranging from 1 µm3 to thousands of µm3 in volume.

4. The method of claim 1, wherein an iBAT cell generated according to condition (i) of claim 1 comprises numerous lipid droplets of sizes ranging from 0.5 µm2 to 1000 µm2 in surface area according to a rectilinear parallel projection, or ranging from 5 µm3 to 10,000 of µm3 in volume.

5. The method of claim 1, wherein an iBAT cell generated according to condition (ii) of claim 1 contains numerous lipid droplets of sizes ranging from 0.1 µm2 to 50 µm2 in surface area according to a rectilinear parallel projection, or ranging from 1 µm3 to 100 µm3 in volume.

6. The method of claim 1, further comprising culturing the iBAT cells under conditions sufficient for proliferation to occur.

* * * * *

UNITED STATES PATENT AND TRADEMARK OFFICE
CERTIFICATE OF CORRECTION

| | | |
|---|---|---|
| PATENT NO. | : 11,390,850 B2 | Page 1 of 1 |
| APPLICATION NO. | : 16/311852 | |
| DATED | : July 19, 2022 | |
| INVENTOR(S) | : Olivier Pourquie and Jerome Chal | |

It is certified that error appears in the above-identified patent and that said Letters Patent is hereby corrected as shown below:

In the Claims

In Column 24, Line 10, Claim 2, delete "Transferin" and insert -- Transferrin --

In Column 24, Line 17, Claim 3, delete "µm2 to" and insert -- $\mu m^2$ to --

In Column 24, Line 17, Claim 3, delete "1000 µm2" and insert -- 1000 $\mu m^2$ --

In Column 24, Line 18, Claim 3, delete "1 µm3" and insert -- 1 $\mu m^3$ --

In Column 24, Line 19, Claim 3, delete "µm3" and insert -- $\mu m^3$ --

In Column 24, Line 22, Claim 4, delete "0.5 µm2" and insert -- 0.5 $\mu m^2$ --

In Column 24, Line 22, Claim 4, delete "1000 µm2" and insert -- 1000 $\mu m^2$ --

In Column 24, Line 24, Claim 4, delete "5 µm3" and insert -- 5 $\mu m^3$ --

In Column 24, Line 24, Claim 4, delete "of µm3" and insert -- $\mu m^3$ --

In Column 24, Line 27, Claim 5, delete "0.1 µm2" and insert -- 0.1 $\mu m^2$ --

In Column 24, Line 27, Claim 5, delete "50 µm2" and insert -- 50 $\mu m^2$ --

In Column 24, Line 29, Claim 5, delete "1 µm3" and insert -- 1 $\mu m^3$ --

In Column 24, Line 29, Claim 5, delete "100 µm3" and insert -- 100 $\mu m^3$ --

Signed and Sealed this
Twenty-fourth Day of January, 2023

Katherine Kelly Vidal
*Director of the United States Patent and Trademark Office*